(12) United States Patent
Campanella et al.

(10) Patent No.: US 11,067,549 B2
(45) Date of Patent: Jul. 20, 2021

(54) DESIGNS FOR ENHANCED RELIABILITY AND CALIBRATION OF LANDFILL GAS MEASUREMENT AND CONTROL DEVICES

(71) Applicant: Loci Controls, Inc., Wareham, MA (US)

(72) Inventors: Andrew Campanella, Somerville, MA (US); Ian Martin, Sharon, MA (US); Joseph G. Michels, New York, NY (US); Nathan Pallo, Somerville, MA (US); Peter Quigley, Duxbury, MA (US)

(73) Assignee: Loci Controls, Inc., Wareham, MA (US)

( * ) Notice: Subject to any disclaimer, the term of this patent is extended or adjusted under 35 U.S.C. 154(b) by 234 days.

(21) Appl. No.: 15/478,583

(22) Filed: Apr. 4, 2017

(65) Prior Publication Data

US 2017/0254196 A1    Sep. 7, 2017

Related U.S. Application Data

(63) Continuation of application No. PCT/US2017/020196, filed on Mar. 1, 2017.
(Continued)

(51) Int. Cl.
*G01N 33/00* (2006.01)
*G01N 1/22* (2006.01)
(Continued)

(52) U.S. Cl.
CPC ......... *G01N 33/0006* (2013.01); *B09B 1/006* (2013.01); *B09B 3/0016* (2013.01);
(Continued)

(58) Field of Classification Search
CPC ................. G01N 1/2247; G01N 33/0006–006
See application file for complete search history.

(56) References Cited

U.S. PATENT DOCUMENTS 3,062,037 A    11/1962    Donner et al.
3,567,387 A    3/1971     Jones
(Continued)

FOREIGN PATENT DOCUMENTS

WO    WO 2006/005014 A2    1/2006
WO    WO 2015/072989 A1    5/2015
WO    WO 2016/010985 A1    1/2016

OTHER PUBLICATIONS

50% CH4, 35% CO2, 15% N2. (n.d.). Retrieved Sep. 25, 2015, from http://www.instrumentdepot.com/50-methane-35-carbon-dioxide-15-nitrogen-c-1_27_472.html (Year: 2015).*
(Continued)

*Primary Examiner* — Alexander A Mercado
(74) *Attorney, Agent, or Firm* — Wolf, Greenfield & Sacks, P.C.

(57) ABSTRACT

An apparatus for sampling landfill gas from a landfill flowing through a pipe. The apparatus may comprise: an enclosure configured to receive a section of the pipe; a gas sampling port in the section of the pipe; at least one sensor device disposed in a region of the enclosure, the at least one sensor being coupled to the section of the pipe through the gas sampling port; and thermal insulation positioned to retain heat from the section of the pipe in the region of the enclosure. A method of operating a landfill gas recovery system. The method may comprise: flowing gas from a well riser pipe through a sampling subsystem to a collection system; and heating a portion of the sampling subsystem with the gas flowing from the well riser pipe to the collection system.

20 Claims, 20 Drawing Sheets

Related U.S. Application Data

(60) Provisional application No. 62/301,922, filed on Mar. 1, 2016.

(51) Int. Cl.
| | |
|---|---|
| *B09B 1/00* | (2006.01) |
| *B09B 3/00* | (2006.01) |
| *E21B 36/00* | (2006.01) |
| *E21B 47/06* | (2012.01) |
| *E21B 47/10* | (2012.01) |
| *E21B 49/08* | (2006.01) |
| *E21B 47/07* | (2012.01) |

(52) U.S. Cl.
CPC ............ *E21B 36/00* (2013.01); *E21B 36/003* (2013.01); *E21B 47/06* (2013.01); *E21B 47/10* (2013.01); *E21B 49/08* (2013.01); *G01N 1/2294* (2013.01); *G01N 33/004* (2013.01); *G01N 33/0036* (2013.01); *E21B 47/07* (2020.05); *E21B 49/0875* (2020.05); *Y02C 20/20* (2013.01); *Y02W 30/20* (2015.05)

(56) References Cited

U.S. PATENT DOCUMENTS

| | | | | |
|---|---|---|---|---|
| 4,026,355 | A | * | 5/1977 | Johnson .................. B09B 1/006 |
| | | | | 166/246 |
| 4,191,541 | A | | 3/1980 | Jenkins |
| 4,227,897 | A | * | 10/1980 | Reed .................... B01D 5/0009 |
| | | | | 165/178 |
| 4,494,380 | A | * | 1/1985 | Cross ........................ F01N 3/00 |
| | | | | 62/3.2 |
| 4,670,148 | A | * | 6/1987 | Schneider ................. B09B 1/00 |
| | | | | 156/250 |
| 4,890,672 | A | | 1/1990 | Hall |
| 5,063,519 | A | * | 11/1991 | Zison ....................... B09B 1/00 |
| | | | | 166/250.01 |
| 5,209,941 | A | * | 5/1993 | Wuest .................. F24C 15/327 |
| | | | | 426/510 |
| 5,223,229 | A | * | 6/1993 | Brucker ..................... A61L 2/07 |
| | | | | 292/36 |
| 5,451,249 | A | | 9/1995 | Spiegel et al. |
| 5,458,006 | A | | 10/1995 | Roqueta |
| 5,665,314 | A | | 9/1997 | Berger et al. |
| 5,681,360 | A | | 10/1997 | Siwajek et al. |
| 5,695,641 | A | | 12/1997 | Cosulich et al. |
| 5,830,262 | A | | 11/1998 | Marchini et al. |
| 6,169,962 | B1 | * | 1/2001 | Brookshire ............... B09B 1/00 |
| | | | | 702/47 |
| 6,196,324 | B1 | | 3/2001 | Giacomino et al. |
| 6,241,950 | B1 | | 6/2001 | Veelenturf et al. |
| 6,591,695 | B1 | * | 7/2003 | Brookshire ............... B09B 1/00 |
| | | | | 73/861.61 |
| 6,595,287 | B2 | | 7/2003 | Fisher |
| 6,611,760 | B2 | | 8/2003 | Bentley et al. |
| 6,749,368 | B2 | | 6/2004 | Ankeny et al. |
| 6,799,477 | B2 | | 10/2004 | Brookshire et al. |
| 6,999,883 | B1 | * | 2/2006 | Brady .................... B09B 1/006 |
| | | | | 702/50 |
| 7,187,299 | B2 | | 3/2007 | Kunerth et al. |
| 7,198,433 | B2 | | 4/2007 | Augenstein et al. |
| 7,243,730 | B2 | | 7/2007 | Casey |
| 7,273,098 | B2 | | 9/2007 | Evans et al. |
| 7,373,976 | B2 | | 5/2008 | Casey |
| 7,387,163 | B2 | | 6/2008 | Seegers et al. |
| 7,448,828 | B2 | | 11/2008 | Augenstein et al. |
| 7,748,450 | B2 | | 7/2010 | Mundell |
| 7,866,921 | B2 | | 1/2011 | Stamoulis |
| 7,950,464 | B2 | | 5/2011 | Atencio et al. |
| 7,972,082 | B2 | | 7/2011 | Augenstein et al. |
| 8,047,276 | B2 | | 11/2011 | Stamoulis |
| 8,168,121 | B2 | * | 5/2012 | Elkins ...................... B09B 1/00 |
| | | | | 422/83 |
| 8,186,211 | B2 | * | 5/2012 | Boult ..................... B09B 1/006 |
| | | | | 73/152.27 |
| 8,840,708 | B1 | | 9/2014 | Morrow et al. |
| 8,924,029 | B2 | | 12/2014 | Nath et al. |
| 9,062,536 | B2 | | 6/2015 | Fischer et al. |
| 10,029,290 | B2 | | 7/2018 | Campanella et al. |
| 10,400,560 | B2 | | 9/2019 | Campanella et al. |
| 10,408,747 | B2 | * | 9/2019 | Schlueter ........... G01N 21/3504 |
| 10,449,578 | B2 | | 10/2019 | Campanella et al. |
| 10,556,259 | B2 | | 2/2020 | Campanella et al. |
| 10,576,514 | B2 | | 3/2020 | Campanella et al. |
| 10,576,515 | B2 | | 3/2020 | Campanella et al. |
| 10,639,687 | B2 | | 5/2020 | Campanella et al. |
| 10,705,063 | B2 | | 7/2020 | Campanella et al. |
| 2001/0005812 | A1 | * | 6/2001 | Brookshire ............... B09B 1/00 |
| | | | | 702/6 |
| 2002/0101718 | A1 | * | 8/2002 | Negishi .................... F28F 3/025 |
| | | | | 361/699 |
| 2003/0000281 | A1 | * | 1/2003 | Ketler ................ G01N 33/0006 |
| | | | | 73/1.06 |
| 2004/0055359 | A1 | * | 3/2004 | Ketler ................ G01N 33/0006 |
| | | | | 73/1.07 |
| 2004/0121201 | A1 | | 6/2004 | Roche et al. |
| 2006/0251540 | A1 | * | 11/2006 | Benning .................... A61L 2/07 |
| | | | | 422/3 |
| 2007/0224085 | A1 | | 9/2007 | Tooley |
| 2007/0225923 | A1 | | 9/2007 | Tooley |
| 2007/0254196 | A1 | * | 11/2007 | Richards ................. F01D 15/10 |
| | | | | 60/39.281 |
| 2008/0011248 | A1 | * | 1/2008 | Cutlip ....................... E21F 7/00 |
| | | | | 123/3 |
| 2008/0127726 | A1 | * | 6/2008 | Elkins ...................... B09B 1/00 |
| | | | | 73/152.42 |
| 2009/0136298 | A1 | | 5/2009 | Augenstein et al. |
| 2010/0310733 | A1 | * | 12/2010 | Hoffman .................. F24C 7/00 |
| | | | | 426/233 |
| 2011/0061439 | A1 | | 3/2011 | Dong et al. |
| 2011/0061874 | A1 | | 3/2011 | Stamoulis |
| 2011/0081586 | A1 | * | 4/2011 | McAlister ................. C25B 1/00 |
| | | | | 429/422 |
| 2011/0132104 | A1 | * | 6/2011 | Benson ...................... G01F 1/40 |
| | | | | 73/861.63 |
| 2011/0198094 | A1 | | 8/2011 | Stamoulis |
| 2011/0231099 | A1 | * | 9/2011 | Elkins ...................... B09B 1/00 |
| | | | | 702/12 |
| 2011/0272420 | A1 | * | 11/2011 | Landess ............ H01L 21/67363 |
| | | | | 220/694 |
| 2012/0191349 | A1 | * | 7/2012 | Lenz .................... G01N 33/0075 |
| | | | | 702/2 |
| 2012/0206715 | A1 | * | 8/2012 | Laub .................... G01N 33/0047 |
| | | | | 356/51 |
| 2012/0287418 | A1 | * | 11/2012 | Scherer ................... G01N 21/61 |
| | | | | 356/51 |
| 2013/0180703 | A1 | * | 7/2013 | Colby ....................... E21B 41/00 |
| | | | | 166/75.13 |
| 2013/0193325 | A1 | * | 8/2013 | Phillips ............... G01N 21/3504 |
| | | | | 250/339.07 |
| 2013/0247647 | A1 | * | 9/2013 | Mahoney ........... G01N 33/2841 |
| | | | | 73/19.11 |
| 2013/0334418 | A1 | * | 12/2013 | Cowie ................. G01N 33/0009 |
| | | | | 250/339.03 |
| 2014/0182846 | A1 | * | 7/2014 | Fischer .................... B09B 1/006 |
| | | | | 166/250.15 |
| 2014/0284935 | A1 | * | 9/2014 | Disbennett ............ F02B 63/042 |
| | | | | 290/1 A |
| 2014/0338878 | A1 | * | 11/2014 | Tessnow ................ F28F 21/084 |
| | | | | 165/185 |
| 2015/0000426 | A1 | * | 1/2015 | Rolston ............... G01N 33/0016 |
| | | | | 73/863.11 |
| 2015/0226045 | A1 | * | 8/2015 | Fischer .................... E21B 43/12 |
| | | | | 166/250.15 |
| 2015/0275632 | A1 | * | 10/2015 | Fischer .................... E21B 43/12 |
| | | | | 166/250.15 |
| 2015/0330938 | A1 | * | 11/2015 | Henson ................. G01N 27/4114 |
| | | | | 205/783 |
| 2015/0354032 | A1 | * | 12/2015 | Yuan ......................... C22C 21/04 |
| | | | | 420/534 |

(56) References Cited

U.S. PATENT DOCUMENTS

| | | | |
|---|---|---|---|
| 2015/0362468 A1* | 12/2015 | Gerhold | G01N 33/0016 73/28.04 |
| 2016/0011159 A1* | 1/2016 | Sekiya | G01N 27/4077 73/23.31 |
| 2016/0025696 A1* | 1/2016 | Birks | G01N 33/0039 250/435 |
| 2016/0033391 A1* | 2/2016 | Stroganov | G01N 21/15 356/326 |
| 2016/0123946 A1* | 5/2016 | Dufresne | G01N 33/0045 356/437 |
| 2016/0169826 A1* | 6/2016 | Youssi | G01N 33/46 324/664 |
| 2016/0209133 A1* | 7/2016 | Hu | B32B 37/06 |
| 2016/0237007 A1* | 8/2016 | Morrow | C10L 3/104 |
| 2016/0238494 A1* | 8/2016 | Chrin, II | G01N 1/2247 |
| 2016/0287870 A1* | 10/2016 | Yip | A61N 1/36038 |
| 2016/0377457 A1* | 12/2016 | Zhang | G01D 9/32 702/130 |
| 2017/0080762 A1* | 3/2017 | Guinart | B60C 23/0476 |
| 2017/0122065 A1 | 5/2017 | Fischer et al. | |
| 2017/0176590 A1* | 6/2017 | Sharonov | G01S 13/64 |
| 2017/0216891 A1 | 8/2017 | Campanella et al. | |
| 2017/0216892 A1 | 8/2017 | Campanella et al. | |
| 2017/0216893 A1 | 8/2017 | Campanella et al. | |
| 2017/0218730 A1 | 8/2017 | Campanella et al. | |
| 2017/0218731 A1 | 8/2017 | Campanella et al. | |
| 2017/0218732 A1 | 8/2017 | Campanella et al. | |
| 2017/0254787 A1 | 9/2017 | Campanella et al. | |
| 2018/0003572 A1* | 1/2018 | Garsd | G01K 3/14 |
| 2018/0003684 A1* | 1/2018 | Kerr | G01N 33/0006 |
| 2018/0024202 A1* | 1/2018 | Erickson | G01R 19/16542 340/636.15 |
| 2018/0154408 A1 | 6/2018 | Ko et al. | |
| 2018/0164137 A1* | 6/2018 | Layher | G01F 1/684 |
| 2018/0171604 A1* | 6/2018 | Kim | B01J 20/3204 |
| 2018/0304323 A1 | 10/2018 | Campanella et al. | |
| 2019/0069245 A1* | 2/2019 | Miller | H04W 52/0261 |
| 2019/0277119 A1 | 9/2019 | Campion | |
| 2019/0277821 A1 | 9/2019 | Quigley et al. | |
| 2020/0086365 A1 | 3/2020 | Campanella et al. | |
| 2020/0101504 A1 | 4/2020 | Quigley et al. | |
| 2020/0101505 A1 | 4/2020 | Quigley et al. | |
| 2020/0130033 A1 | 4/2020 | Campanella et al. | |
| 2020/0197990 A1 | 6/2020 | Quigley et al. | |
| 2020/0254497 A1 | 8/2020 | Campanella et al. | |
| 2020/0306806 A1 | 10/2020 | Quigley et al. | |
| 2020/0306807 A1 | 10/2020 | Quigley et al. | |

OTHER PUBLICATIONS

International Search Report and Written Opinion for International Application No. PCT/US17/28818 dated Sep. 8, 2017.
[No Author Listed], Cloud-Based Wellwatcher Analytics Platform Offers 24/7/365 Visibility on Landfill Gas-Collection Systems. Tech Note. Loci Controls. Nov. 2016. 1 page.
[No Author Listed], Increase Landfill Gas Collection by Up to 30%. Tech Note. Loci Controls. Oct. 2016. 1 page.
[No Author Listed], Loci Controller Combines Active Flow Control With 24/7/365 Real-Time Gas-Composition Analysis to Maximize Landfill Gas Extraction. Tech Note. Loci Controls. Nov. 2016. 1 page.
[No Author Listed], Loci Sentry Utilizes Passive Flow and Gas-Composition Monitoring in Conjunction With Loci Controller and Wellwatcher Analytics to Maximize Landfill Gas Collection. Tech Note. Loci Controls. Nov. 2016. 1 page.
[No Author Listed], Methacontrol® Optimizing landfill gas recovery. Oct. 9, 2013. http://www.veolia.com/en/veolia-group/media/news/methacontrol-r 1 page.
Bieker et al., Real-Time Production Optimization of Offshore Oil and Gas Production Systems: A Technology Survey. SPE International. 2006. 8 pages.
Xu et al., Impact of changes in barometric pressure on landfill methane emission. AGU Publications. Jul. 10, 2014. 17 pages.
PCT/US2017/020196, Jun. 7, 2017, International Search Report and Written Opinion.
PCT/US17/28818, Jul. 10, 2017, Invitation to Pay Additional Fees.
International Search Report and Written Opinion for International Application No. PCT/US2019/020251 dated May 31, 2019.
Fay et al., Remote Real-Time Monitoring of Subsurface Landfill Gas Migration. Sensors. 2011;11(7):6603-29.
U.S. Appl. No. 16/290,387, filed Mar. 2, 2019, Quigley et al.
U.S. Appl. No. 16/510,167, filed Jul. 12, 2019, Hale et al.
PCT/US2019/020251, May 31, 2019, International Search Report and Written Opinion.
U.S. Appl. No. 16/694,745, filed Nov. 25, 2019, Campanella et al.
PCT/US2019/054013, Dec. 4, 2019, International Search Report and Written Opinion.
U.S. Appl. No. 16/589,372, filed Oct. 1, 2019, Quigley et al.
U.S. Appl. No. 16/589,391, filed Oct. 1, 2019, Quigley et al.
EP 17760717.3, Oct. 2, 2019, Extended European Search Report.
Extended European Search Report for European Application No. 17760717.3 dated Oct. 2, 2019.
Collins et al., Web-based monitoring of year-length deployments of autonomous gas sensing platforms on landfill sites. 2011 IEEE Sensors Proceedings. 2011. 1620-3.
International Search Report and Written Opinion for International Application No. PCT/US2019/054013 dated Dec. 4, 2019.
U.S. Appl. No. 16/726,323, filed Dec. 23, 2019, Campanella et al.
U.S. Appl. No. 16/831,131, filed Mar. 26, 2020, Campanella et al.
U.S. Appl. No. 16/745,892, filed Jan. 17, 2020, Campanella et al.
U.S. Appl. No. 16/901,405, filed Jun. 15, 2020, Quigley et al.
U.S. Appl. No. 16/901,430, filed Jun. 15, 2020, Quigley et al.
U.S. Appl. No. 16/927,471, filed Jul. 13, 2020, Quigley et al.
U.S. Appl. No. 16/927,479, filed Jul. 13, 2020, Quigley et al.
U.S. Appl. No. 16/927,482, filed Jul. 13, 2020, Quigley et al.
U.S. Appl. No. 16/927,488, filed Jul. 13, 2020, Quigley et al.
Extended European Search Report for European Application No. 17906368.0 dated Oct. 15, 2020.
International Search Report and Written Opinion for International Application No. PCT/US2017/020196 dated Jun. 7, 2017.
Invitation to Pay Additional Fees for International Application No. PCT/US17/28818 dated Jul. 10, 2017.

* cited by examiner

DESIGNS FOR ENHANCED RELIABILITY AND CALIBRATION OF LANDFILL GAS MEASUREMENT AND CONTROL DEVICES

RELATED APPLICATIONS

The present application claims the benefit under 35 U.S.C. § 365(c) and § 120 and is a continuation (CON) of PCT International Application PCT/US2017/020196, filed Mar. 1, 2017, and titled "DESIGNS FOR ENHANCED RELIABILITY AND CALIBRATION OF LANDFILL GAS MEASUREMENT AND CONTROL DEVICES" which claims priority under 35 U.S.C. § 119(e) to U.S. Provisional Application Ser. No. 62/301,922, filed on Mar. 1, 2016, and titled "DESIGNS FOR ENHANCED RELIABILITY OF LANDFILL GAS MEASUREMENT AND CONTROL DEVICES". Each of the above-identified applications is hereby incorporated by reference in its entirety.

FEDERALLY SPONSORED RESEARCH

This invention was made with government support under SBIR Phase II Award No. 1632439 awarded by the National Science Foundation. The government has certain rights in the invention.

BACKGROUND

Landfills typically produce landfill gas (LFG) as a result of decomposition processes of organic waste, and methane is often a component of LFG. In order to reduce emissions of methane and other contaminants in LFG, the landfill sites are typically capped with a layer of cover material and gas extraction systems are installed to pull LFG out before it can penetrate the cover layer and escape. At larger sites, these gas extraction systems can consist of a plurality of vertical and horizontal wells drilled or constructed into the landfill, which are connected with piping to one or more vacuum sources. The cover layer prevents gas from freely escaping, while the vacuum in the extraction wells pulls LFG into the collection system. LFG extraction wells typically have a manual valve that adjusts the localized vacuum pressure in that well, as well as a set of ports for sampling the gas characteristics with a portable gas analyzer. Landfill gas is most often disposed of in a flare, processed for direct use, or used to power electricity generation equipment (such as generators or gas turbines).

The horizontal and vertical wells in the collection system typically consist of a length of perforated pipe connected to a length of solid pipe that rises through the surface of the landfill for wellhead access. The perforated pipe may be laid across the landfill during active dumping and subsequently buried (forming "horizontal wells") under additional lifts or inserted into a hole drilled through the landfill (traditional "vertical wells"). This pipe then acts as the gas extraction interface between the fill and the collection system. Additional extraction points may also exist, with collection through leachate cleanouts, sumps, cisterns, temporary cover layers, and other points of fluid connection with the landfill mass.

SUMMARY

Some aspects include an apparatus for sampling landfill gas from a landfill flowing through a pipe, the apparatus comprising: an enclosure configured to receive a section of the pipe; a gas sampling port in the section of the pipe; at least one sensor device disposed in a region of the enclosure, the at least one sensor being coupled to the section of the pipe through the gas sampling port; and a wireless transmitter. In some embodiments, the apparatus may include thermal insulation positioned to retain heat from the section of the pipe in the region of the enclosure.

Further aspects include an apparatus for sampling landfill gas from a landfill flowing through a pipe, the apparatus comprising: a sampling subsystem comprising: a gas inlet port and a gas outlet port; a region configured to receive a section of the pipe, the section of the pipe having a gas sampling port; a thermoelectric condenser; at least one gas sensor coupled to the gas outlet port; and a gas flow passage from the gas inlet port to the gas outlet port, the gas flow passage passing adjacent to and in thermal contact with the thermoelectric condenser.

Additional aspects include an apparatus for sampling landfill gas from a landfill flowing through a pipe, the apparatus comprising: an orifice block comprising: a gas inlet port and a gas outlet port; a region configured to receive a section of the pipe, the section of the pipe having a gas sampling port; and a gas flow passage from the gas inlet port to the gas outlet port, the gas flow passage comprising at least one fluid knock-out. The apparatus may also include a filter for at least one of a particulate and/or a corrosive gas.

Additionally, some aspects include a method of operating a landfill gas recovery system, the method comprising: flowing gas from a well riser pipe through a sampling subsystem to a collection system; and heating a portion of the sampling subsystem with the gas flowing from the well riser pipe to the collection system.

In some embodiments, specially designed consumable or reusable filter hardware and/or features may be employed to actively or passively treat gas that is drawn in and sampled from the LFG stream or atmosphere port, including adsorbent or absorbent filter media, active condensation elements, particulate filters, or screens or knock-outs.

Some embodiments may employ geometrically advantageous designs to ensure water does not accumulate within the sampling system, for instance by reducing water traps or assuring gravity assists drainage of liquids wherever possible.

In some embodiments, hardware and methods may be employed to allow for easy field calibration of sensors.

In some embodiments, specially designed features in the orifice plate, the slot into which the orifice plate is inserted, and the lid that seals the orifice plate into the pipe carrying the gas stream may be employed to mitigate manufacturing variations and concerns when measuring flow.

Some embodiments may measure the pressure at specific locations in the LFG stream to address limitations in sensing hardware and improve system telemetry and control.

In some embodiments, a combination of active and/or passive measures may be employed to maintain an internal temperature within operating limits.

Some embodiments may employ a front panel used for service tasks such as accessing consumable or replaceable filter elements, connecting an external gas source for calibration, interacting with a user interface to control measurement, calibration, and control commands.

Some embodiments may be designed to have specific mechanical features and/or be designed for a specific mounting strategy to address the variety of well styles across different landfills.

Some or all of the components of an apparatus comprising sensors may be formed of a polymeric material. These components may include a region configured to receive a section of pipe and one or more gas flow passages. The polymeric material may be thermoplastic, thermoset, urethane or a co-polymer, which could be CPVC or HDPE. In some embodiments, an apparatus comprising a sensor may include a port or other connection to a source of gas of known composition, which may serve as a calibration gas. The apparatus may be controlled to supply calibration gas to a sensor chamber for making measurements that may be used to calibrate the measurement hardware. One source of a gas of known composition is a source of air, such as the ambient environment. In some embodiments, the at least one source gas of known composition is a source of a mixture of $CO_2$ and $CH_4$. In other embodiments, the at least one source gas of known composition contains a mixture of two gasses of known composition. Alternatively, the least one source of a gas of known composition may be a source of air and a source of a mixture of two gasses of known composition. Such a mixture of two gasses of known composition may comprise at least of $CO_2$ and $CH_4$.

Some embodiments may be designed to have specific features that allow for easier handling, installation, and removal of units at a specific site.

DETAILED DESCRIPTION

Figure 1:
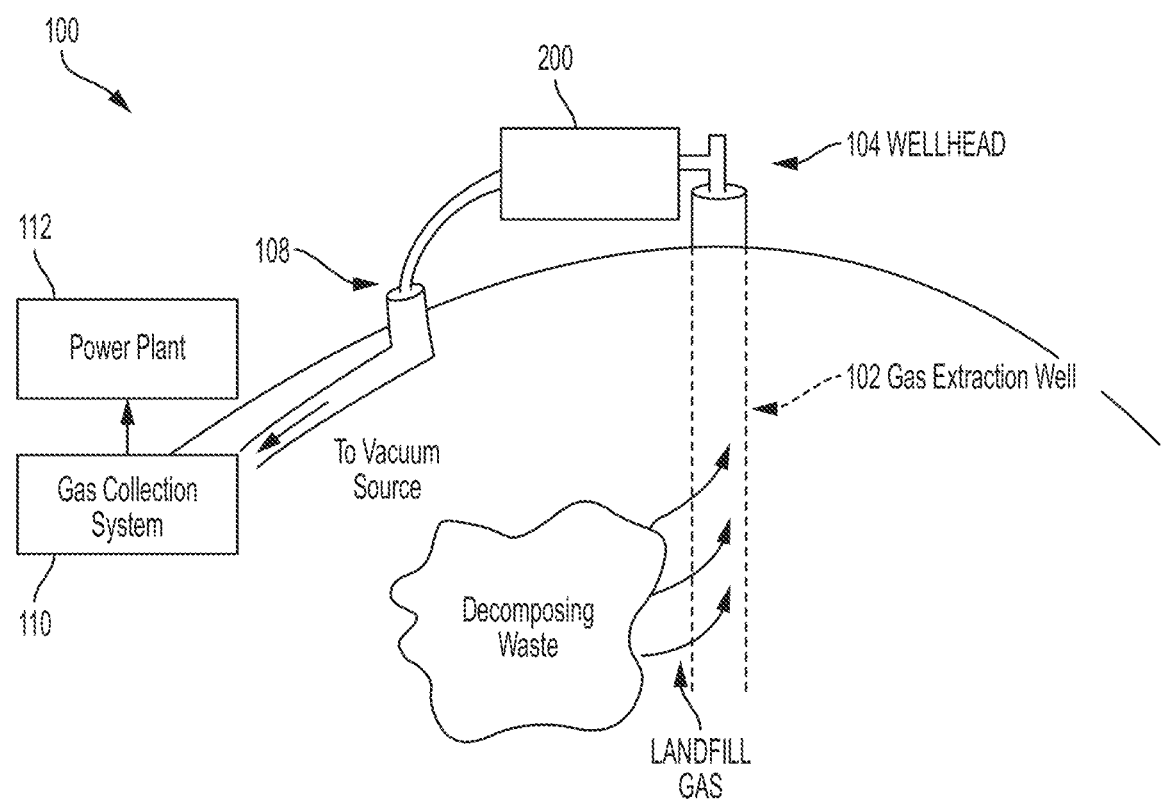
FIG. 1 is a sketch illustrating a landfill gas extraction system, according to some embodiments.

The inventors have recognized and appreciated that equipment and methods for improving the reliability of sensing the characteristics of the LFG at some or all extraction points improves extraction of LFG. For example, insufficient vacuum pressure in a given extraction well can lead to the buildup of gas underground, and may result in fugitive emissions as excess gas permeates the cover of the landfill and escapes into the atmosphere. Excessive vacuum can similarly pull atmospheric oxygen into the waste mass, upsetting the anaerobic conditions that are necessary for methane generation, and if left uncorrected, may lead to elevated subterranean temperatures and a variety of associated problems (including, but not limited to, ground instability, damage to the collection infrastructure, runaway exothermic reactions, odors, and the release of toxins and other chemicals that might otherwise remain trapped underground). As environmental and other conditions in the landfill change, the rates of gas generation and extraction can become unbalanced, requiring an adjustment of the extraction pressure in order to avoid the problems above. Additionally, tight control of the gas collection system can be used to ensure the optimal or maximum energy production when the gas is used as a renewable resource, with the benefit of minimizing the amount of fugitive gas emissions into the atmosphere. Furthermore, modelling and estimating production (for instance, for predicting existing capacity in energy markets or potential capacity for capital investment), or otherwise determining the appropriate set-point of generating capacity or direct use during operation, requires sensing of these characteristics of gas generation and extraction.

The inventors have developed landfill gas control and measurement device that improves the efficiency of landfill gas extraction. This system, called WellWatcher, includes units that may be installed in-line with the landfill gas collection system, typically serving as the connection between the wellhead (well riser) and the extraction system (vacuum riser). A system comprised of a plurality of these units is meant to alleviate the need for a constant presence of dedicated personnel attending to each wellhead, so it may be advantageous that the hardware perform reliably with minimal need for maintenance and technician attention.

Such units may contain wetted sensors (sensors that require a fluid connection with the gas stream or a sample of the gas to perform the desired function—including pressure sensors and gas composition sensors that require immersion in the media). The inventors have recognized and appreciated that such sensors are particularly at risk of degrading or failing to operate properly. They have implemented specific accommodations in the design and construction of such units to mitigate the particulate, humidity, and corrosive properties of a landfill gas stream to extend the lifetime and accuracy of any wetted sensors. Furthermore, as this hardware may typically be installed outdoors, certain system design aspects and enclosure considerations may also be implemented to ensure the internal components remain within acceptable operating conditions, such as staying above freezing when external temperatures are sub-zero in winter months. An additional consideration recognized and addressed by one or more of the embodiments described herein, is that this device have access panels, thoughtful mounting features and an adequate strategy for rapid deployment and replacement in the field to minimize effort required during installation and time spent during service, scheduled maintenance, replacement, and uninstallation.

The inventors have recognized and appreciated that a more reliable and cost effective LFG extraction system may be achieved with such an improved sampling unit. A sampling unit may have features that enable it to operate reliably in the harsh environment of a landfill, which can involve low temperatures and corrosive gas. To provide such a system, the inventors have recognized and addressed, in one or more of the embodiments described herein, problems, such as:

LFG exiting a well is typically 99⁺% humidity and may contain particulate, corrosive or caustic constituents.

Condensate or other liquids accumulating or flowing within the gas extraction system pose an aspiration or ingress risk to sensing systems that draw a gas sample from this extraction system.

Sensors may need to interact with this gas to measure characteristics including, but not limited to, pressure, flow, gas composition, humidity, temperature, etc.

Sensors may contain sensitive electronics, optical components, or otherwise lack protection against LFG constituents, including liquids such as condensate, or corrosion.

Pipes or tubes conveying LFG to the sensing locations (for example, to a port of a pressure sensor or to a non-dispersive infrared (NDIR) detector) may become clogged from LFG condensate or particulates accumulating within these tubes, inhibiting sensor functionality.

Appropriate filters that might mitigate some or all of the harmful effects of LFG on an LFG measurement system may be bulky and difficult to integrate inline or in a small form-factor device, difficult to replace or service, costly to implement, and often require a specific orientation with respect to gravity for correct operation.

Sensors, in particular gas composition sensors (NDIR, fluorescence, etc.), often require calibration with one or more references points. For instance, given controlled test conditions (such as calibration gasses of known composition), a two-point calibration might find the difference between expected reading and actual reading of a sensor at zero and at the rated range of the sensor to calculate a calibration offset and gain that are then used to compensate and improve sensor accuracy of future measurements.

Sensor measurements, in particular gas composition sensors (NDIR, fluorescence, etc.), often exhibit dependence or sensitivity to factors such as sample gas pressure, temperature, humidity, and residence time.

It is desirable for sensor calibration to occur under the same conditions—such as pressure, temperature, or sample gas flow—as would occur during a normal measurement cycle.

The measurement and control hardware is typically deployed outdoors, and may need to survive extreme weather—especially sub-freezing temperatures.

It is desirable for certain sensing elements, such as an orifice plate used for flow measurement, to be accessible and interchangeable without disassembling the equipment; flow measurement range is dictated by the size of the orifice and the range of the differential pressure sensor that measures the pressure across this orifice. If the pressure sensor range is fixed, field adjustment to the flow measurement range when flow is over or under limits initially assumed—or as flow increases or decreases over the lifetime of the well—may only be possible by swapping orifice plates to better match differential pressure to the measurement range of the pressure sensor. A field-interchangeable orifice plate, as described herein, enables such a field adjustment such that the pressure drop across the orifice plate falls within the range of the pressure sensor for any installation.

It is desirable for certain consumables, such as gas filtration elements, to be accessible and replaceable without disassembling the unit—for instance, allowing a technician to replace an expired, fully consumed, or clogged filter with a fresh one.

Health and diagnostics of certain components, such as consumable filter health, should be measured or inferred and reported so as to alert technicians of maintenance needs and inform hardware lifetime planning.

It may be desirable for wetted components (those components interfacing with LFG, sampled or otherwise) to be sealed or otherwise configured to prevent ingress of LFG into the enclosure of the measurement and control device, or egress of LFG into the atmosphere where it can cause an environmental or safety concern.

It may be desirable for components to be manufacturable and assembled or connected as easily as possible.

It may be desirable for field installation, replacement, and removal of the hardware to be easy, quick, and robust.

It may be desirable for installation orientation to be selected for best performance of internal elements, such as water knock-outs or sensors, and best control of condensate flow—for instance, to direct flow through an orifice eccentricity and/or away from gas sample inlet ports.

It may be desirable to reduce the impact of installation to existing infrastructure—for instance, eliminating any needs to modify existing wellheads, piping, or other components.

Dust, humidity, precipitation, insects, and other detritus are likely to be present in the environment, so it may be desirable for equipment design to consider these factors and to mitigate them.

The inventors recognized and appreciated techniques to address some or all of these concerns and problems associated with measuring the properties of LFG and controlling the extraction process. The properties that may be measured and/or controlled include, but are not limited to, flow, temperature, pressure, and gas composition. One or more sensors may be included to measure one or more of these characteristics of the gas or of the gas flow. Described herein are embodiments for components of a system that controls the extraction of LFG at the point of installation of those components, are survivable when deployed in a harsh environment like a landfill wellfield, and/or enable reduction in the effort and time associated with installing and maintaining field units.

Overview of System Elements

Any suitable combinations of one or more of the following elements may be implemented in various embodiments of a system as described herein.

LFG Connection—any point in the LFG recovery system that a unit may be connected to. This could include, but is not limited to, the wellhead, the system vacuum riser, buried or above ground pipes, junctions, flares, blowers, generators or engines, coalescers, filters, pumps, valves, leachate systems, or digesters.

Port—an opening in a connection, pipe, vessel, valve, chamber, or the like through which air or gas flow or pressure may pass. The port may have features such as threading, barbs, or quick-connect geometries or fittings for external connections or jumpers, gaskets, sealing with Teflon tape, or other features. One of the functions of some embodiments is to make and break connections between two or more ports, with one or more ports acting as pressure or vacuum sources, flow inlets/intakes or outlets/exhausts, or sensor interfaces. When a port is referred to in the context of a valve, the port may either be open (connected to one or more other ports integral to the valve) or closed (blocked, obstructed).

Pressure—the amount of force exerted over an area, specifically by a gas in some embodiments. Pressure may or may not be associated with a corresponding flow in some embodiments. For example, when measuring static pressure, or the pressure (vacuum) within the LFG vacuum system compared to atmospheric pressure, with a diaphragm pressure sensor, no steady-state flow should be passing through the pressure sensor through its connections to the LFG system. While there may be a transient flow during the initial connection between two ports such as this, an important behavior of such a connection that may be found in some embodiments is to convey pressures between ports and not flow of a gas, and it may be specifically referred to as such: a connection or direction of pressures.

Additionally, other pressure measurements may be used to infer a flow in the vessel that they are connected to, but again such measurements may be made with minimal steady-state flow through the corresponding measurement ports. This is the case with either differential pressure measurements, where pressure is sensed on both sides of a constriction or orifice in the flow path and where at least two pressures may be directed to the corresponding pressure sensor ports, or with single-ended or impact pressure measurements, such as with a pitot, where a single pressure corresponding to the flow in the vessel may be directed to the pressure sensor port.

In cases where connections become obstructed (by condensate, particulate matter, etc.), inhibiting a unit's ability to connect either pressure or flow between ports, a transient pressure may be applied by the unit to clear the blockage. The unit may include a controller, which may receive outputs of sensors indicating such a condition and, in response, generate control signals for valves or other actuators to apply a pressure differential across the blockage. Such a function may be achieved, for example, by connecting one port of the blocked connection to the LFG vacuum and the other to atmosphere. Such control operations would, in this case, yield a pressure transient across the ports that gives way to a steady-state flow once the blockage is cleared. Alternatively, the unit may produce such a pressure by activating a pump on one side of the blockage. Again, the behavior in this case would yield a pressure transient across the ports of the blocked connection that gives way to a steady-state flow once the blockage is cleared. The cleared tube could then be connected as needed to direct pressure or flow unobstructed as desired (and the pump, if used, could be disengaged).

Pressure may also be described in the context of a steady-state flow within some embodiments. Narrow diameters of connections, valves, ports, or other orifices within the unit may create pressure drops during flow of gas. For example, the flow of sample gas into or out of the sample chamber may increase or decrease the pressure within the chamber. The pressure associated with the flow of gas within the unit may be used to infer the rate of flow, determine the presence of clogs, or to augment certain sensor readings or otherwise provide utility.

Sensor—typically an electronic component that converts a physical property, such as temperature, pressure or gas composition, into another form, such as electrical (analog or digital) representation or signal.

Figure 10:
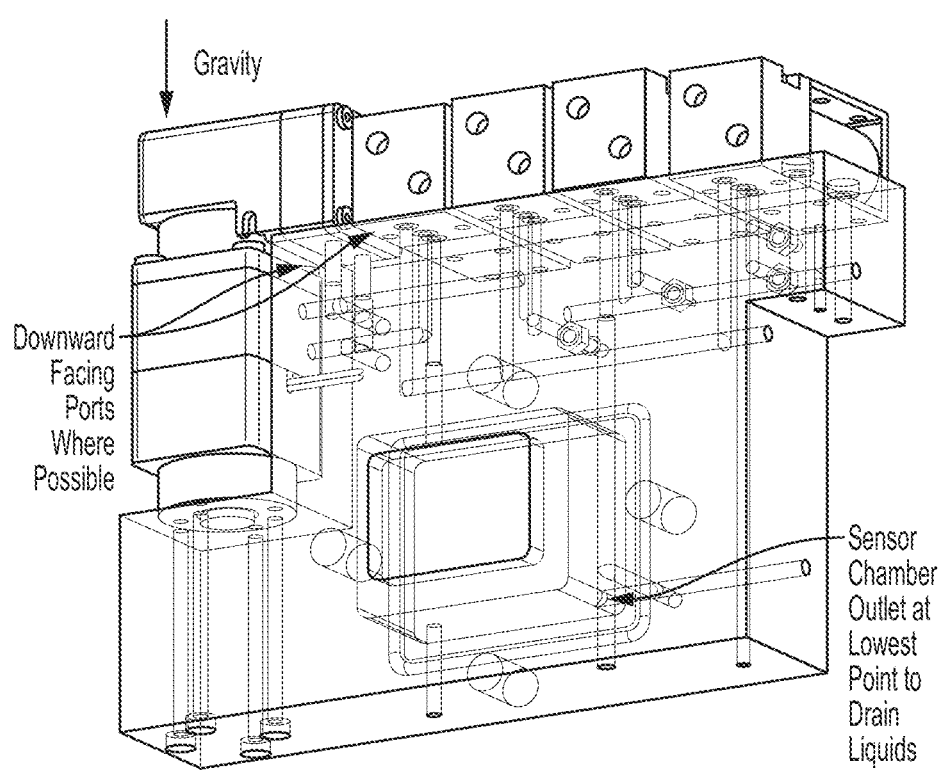
FIG. 10 is a diagram illustrating a manifold, according to some embodiments.

Sensor chamber—an enclosed volume within the unit that contains one or more sensors. A sample gas or purge (clean) gas or air may be passed through the chamber through one or more ports, either in a metered (fixed volume) or continuous flow. The sensors within this chamber may measure one or more characteristics of the gas passed through the chamber (temperature, humidity, pressure, composition, etc.). Additionally, the sensors may be integrated into the sensor chamber construction (for instance, light emitters or detectors, sensor optics, gratings or filters, semiconductors, gas filters, etc.) may be incorporated into a wall, face, boss, lid, or other feature of the chamber. Sensors may also be housed or seated on a circuit board that is either placed within the chamber or that acts as a face or lid of the sensor chamber. The sensor chamber may have a lid that is removable for service, sensor replacement, or other actions requiring entry into the chamber. An example is shown in FIG. 10.

Valve—a mechanical or electromechanical device capable of opening or closing, either completely or partially, a connection between two or more ports. In some embodiments, valves described herein may be controlled by signals output by a controller within or coupled to the unit, allowing automated performance of functions described herein based on programming or other configuration of the controller.

Solenoid valve—an electromechanical device capable of opening or closing a connection between two or more ports when triggered by an electronic signal. The solenoid valve may be referred to simply as a solenoid. This valve may also be used to redirect flow or pressure by simultaneously opening the connection between one port and another port, while closing the connection between the first port and a third. The solenoid may also have additional states or positions (configuration of port to port connections), where several ports can be open or connected to each other, or some or all ports can be closed. The states may be momentary, requiring the electronic signal to be maintained for the duration of the state, or latched, maintaining state after an electronic signal.

Upstream Pipe—a component that feeds gas from the wellhead to a unit. In some embodiments, the upstream pipe may pass through the enclosure of the unit and may be connected to one end of an electromechanical control valve in any suitable way. According to some embodiments, the pipe may be solvent welded to a union that mates with the electromechanical control valve. In some embodiments, this union may be drilled and tapped ¼-NPT for a stainless steel thermistor. This thermistor may measure the temperature of the landfill gas and may be constantly immersed in the flow. Additionally, this pipe may have a slot for a configurable acrylic orifice plate, as well as a port drilled on each side of the slot for measuring pressure and drawing gas composition samples, according to some embodiments.

Orifice Block/Curved Bolted Block—a member that may serve as a mechanical support for some or all of the components described herein. In accordance with some embodiments, the orifice block may be of unitary construction, but in other embodiments, one or more components may be attached to form an orifice block. The orifice block may have integrally formed therewith, or may have coupled to it, one or more elements that enable functions described herein. In some embodiments, the orifice block may mate with the upstream pipe using dynamic seals (O-rings, gaskets) with compression applied using, in some embodiments, a U-bolt, or static seals using solvent or thermal welds or epoxies. According to some embodiments, the front face (opposite from the pipe) may feature an orifice lid that can be opened, allowing a technician to change the orifice plate. Additionally, this face may contain three quick connect ports. The two quick connect ports at the left of the orifice lid may allow for a technician to install and remove a disposable filter. The single quick connect to the right may be a provision for a gas calibration port.

In some embodiments, the orifice block may include a manifold, comprising one or more passageways through which gas may flow. Inputs and outputs of these passages may be connected to components of the sampling subsystem containing the manifold. The manifold may include controllable valves such that gas may flow from selected one or ones of the inputs to selected one or ones of the outputs to configure the sampling subsystem for any of a number of operations, including sampling, calibration, purging, etc. When the manifold is configured for gas sampling, gas may be drawn in through the upstream port, which in the illustrated embodiment serves as the gas inlet port 236, (at the well side of the orifice plate), through an integrated water knock-out, across a thermoelectric-chilled cold plate condenser maze on the top of the block, back into the block to the bottom left quick connect port, out through the port into an external H2S adsorbent media filter and a particulate filter, back into the top left quick connect port, and into the manifold, according to some embodiments. Additionally, the exhaust of this sample gas may return from the manifold back into the orifice block and out the downstream port, which in the illustrated embodiment serves as the gas outlet port 238, (on the valve/union/thermistor side of the orifice plate). When the manifold is configured for pressure sensing, no flow may occur; instead, differential pressure may be measured through the fluid connection of a differential pressure transducer to the upstream and downstream ports, while a static pressure measurement may be made from a separate transducer teed off of the upstream differential transducer connection, according to some embodiments. Portions of the apparatus, such as the orifice block and gas flow passages, may be formed of a polymeric material. Portions formed of the polymeric material may include the entire enclosure, a region configured to receive the section of pipe or some or all of the gas flow passages. The polymeric material may be thermoplastic, thermoset, urethane or a co-polymer. In some embodiments, the polymeric material may be CPVC or HDPE.

Manifold and Solenoid Valves—allows multiple valves, four in some embodiments, to reconfigure the fluid connections so both pressure measurements and gas samples, as well as purge cycles meant to eject condensate from the upstream and downstream ports on the orifice block. The valves, in combination with one or more pumps, may be controlled to implement a measurement cycle to control sensing of LFG or calibration gas, purge the system, and/or perform other actions. The manifold may also have barbed fittings that are used to convey the differential pressure and static pressure measurements to pressure transducers in the device.

Sample Pump—in some embodiments, differential pressure across the orifice plate may not be enough to fill the sensor chamber during a sample cycle, and because gas sensors may not survive direct and continuous exposure to the gas stream, a sample pump may be used to draw a timed sample of landfill gas from the pipe, through a filtration system, into the sensor chamber. The manifold then may reconfigure so this same pump draws in a clean air sample, purging the gas collection system. In some embodiments, the manifold can be reconfigured so the single pump can purge both upstream and downstream with clean air, as well as pump a sample from the upstream to the downstream port via the sensor chamber.

Downstream Pipe—feeds from the electromechanical valve through an enclosure of the unit to the vacuum/extraction system. According to some embodiments, the pipe may be solvent welded to a union that mates with the electromechanical control valve. Additionally, this union may be drilled and tapped ¼-NPT for a polypropylene barb that conveys the available vacuum pressure to a pressure transducer in the unit measurement and control device.

Available Vacuum—typically refers to the vacuum available on the vacuum riser serving a single well or plurality of wells at the extraction point, whether naturally occurring or created by a blower or other machine. The available vacuum may be the vacuum pressure downstream of the control valve, and representative of the maximum vacuum that could be applied to the extraction point if the valve were fully opened. Available vacuum may be representative of the site-wide system vacuum, but typically less due to pressure drops that occur across the pipes that convey system vacuum to each extraction point System Vacuum—typically refers to the site-wide extraction vacuum pressure created by a blower at the flare, generator or other destruction device. While a single blower may be used to create the extraction for a given site, some wellfields may employ multiple vacuum sources, such that system vacuum may refer to the individual vacuum systems or the sum of all vacuums applied to the wellfield.

LFG Stream—feeds from the electromechanical valve through the box to the vacuum/extraction system. According to some embodiments, the pipe carrying the LFG stream may be solvent welded to a union that mates with the electromechanical control valve. Additionally, this union may be drilled and tapped ¼-NPT for a polypropylene barb that conveys the available vacuum pressure to a pressure transducer in the device.

Applied Vacuum—indicates the amount of vacuum created by a vacuum/extraction system.

Fluid—a liquid, vapor, gas, or combination of any or all.

Fluid Connection—any connection between volumes through which a fluid may flow or pressure may be conveyed.

Exemplary System

FIG. 1 illustrates a landfill gas extraction system 100, according to some embodiments. In some embodiments, a landfill gas extraction system 100 may include one or more gas extraction wells 102 coupled to one or more wellheads 104. In some embodiments, each wellhead may be in fluid communication with a single, corresponding well. This well may be one of any number of wells in a system of wells (not shown). Each well may have one or more of the following components.

In some embodiments, the landfill gas extraction system 100 of a given well may include a gas extraction piping system 108 coupling the well(s) 102 to a gas collection system 110, and one or more sampling units 200 for sampling the landfill gas. In some embodiments, gas collection system 110 may supply the extracted landfill gas to a gas-to-energy power plant 112, which may convert the landfill gas into electrical power (e.g., by burning the landfill gas to turn the rotor of a generator or turbine).

In some embodiments, a control mechanism may operate to improve gas extraction efficiency and/or to control the extraction process for a variety of desired outcomes. Control may be implemented in one or more processors, which may be on one or more printed circuit boards. Those processors may be implemented in one or more of the units 200. In other embodiments, the processors may be separate from units 200 containing sensors, but may be in communication, using known wireless or wired communication channels, with the units 200, for example, by acting as an external device, such that measurements made with the sensors may be communicated to the processors. Accordingly, each of the units 200 may include a wireless transmitter and/or wireless receiver 280.

The control mechanism may control a control valve, discussed further below. According to some embodiments, a central controller 275 may communicate with the control mechanism and the unit 200 of each well in a well system. The central controller 275 may transmit commands to and receive information from the control mechanism of each well.

Examples of control mechanisms and systems according to some embodiments are described in U.S. Provisional Application Ser. No. 61/899,828, titled "In-Situ Control Mechanisms for Landfill Gas Extraction Wells" and filed on Nov. 4, 2013, U.S. Provisional Application Ser. No. 61/913,628, titled "System and Methods for Optimizing Landfill Gas Extraction" and filed on Dec. 9, 2013, and U.S. application Ser. No. 14/532,807, titled "Devices and Techniques Relating to Landfill Gas Extraction" and filed on Nov. 4, 2014, each of which is hereby incorporated by reference herein in its entirety.

Figure 2:
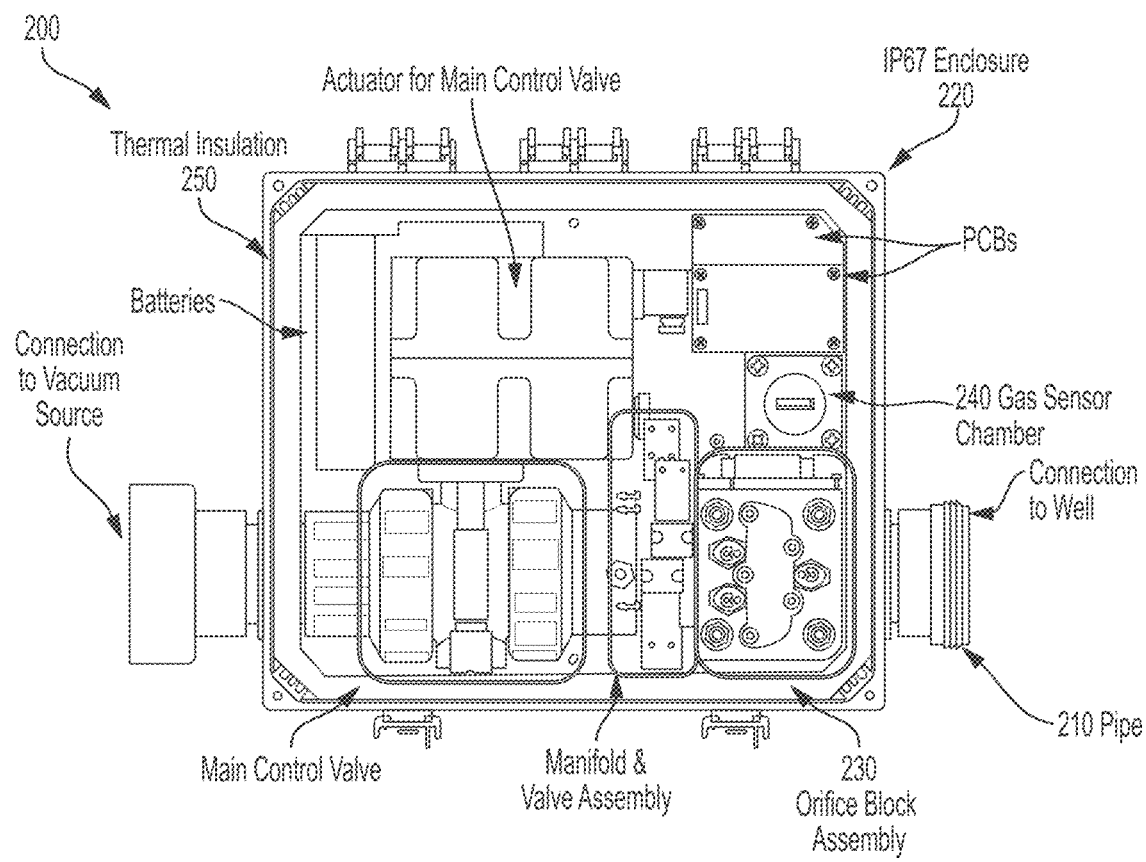
FIG. 2 is a diagram illustrating an exemplary sampling unit, according to some embodiments.
Figure 2A:
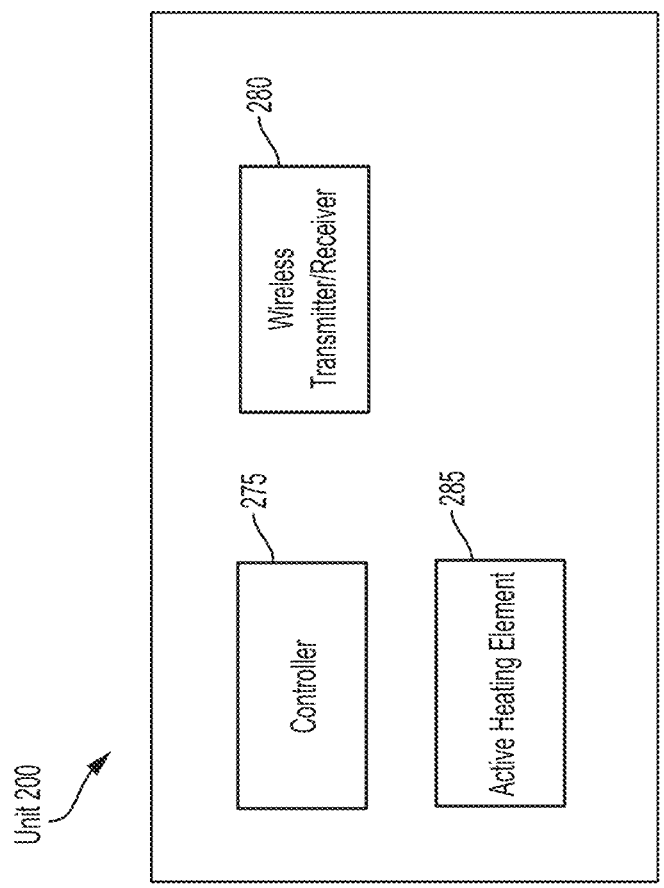
FIG. 2A is a schematic diagram of the exemplary sampling unit of FIG. 2, according to some embodiments.
Figure 16:
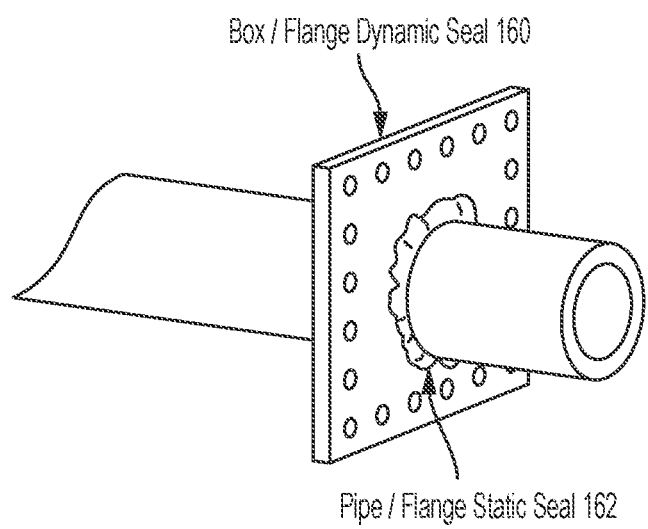
FIG. 16 is a sketch illustrating a flange/pipe seal with a pipe, according to some embodiments.

FIG. 2 illustrates a sampling unit 200 for sampling landfill gas from a landfill flowing through a pipe 210 according to some embodiments. In some embodiments, the unit 200 may include an enclosure 220 configured to receive a section 215 of the pipe 210. According to some embodiments, the enclosure 220 may comprise an hermetic seal (as shown in FIG. 16, dynamic and static seals 160, 162), sufficiently blocking the flow of air and/or other gasses and/or fluids that one of skill in the art would consider the enclosure to be air-tight or water-tight.

According to some embodiments, the enclosure 220 may enclose a sampling subsystem 225. The sampling subsystem 225 may include a support, such as the orifice block 230 or the enclosure 220 itself. Additionally, the sampling subsystem 225 may include a gas inlet port 236 and a gas outlet port 238 mechanically coupled to the support. The sampling subsystem 225 may also include a region 222 mechanically coupled to the support and configured to receive the section 215 of the pipe 210 having the gas sampling port. Additionally, the at least one sensor device may be coupled to the gas outlet port 238.

According to some embodiments, the sampling subsystem 225 may include a thermoelectric condenser 234, which is described in more detail below. Additionally, the sampling subsystem 225 may include a gas flow passage 237 from the gas inlet port 236 to the gas outlet port 238. The gas flow passage 237 may pass adjacent to and may be in thermal contact with the thermoelectric condenser 234.

According to some embodiments, the section 215 of the pipe 210 is coupled to a riser pipe of a well 102 in a landfill such that landfill gas from the well 102 flows through the section 215 of the pipe 210.

According to some embodiments, the unit 200 may also include an orifice block assembly 230. The orifice block 230 may be disposed in the enclosure 220, as shown in FIG. 2. Additionally, the orifice block 230 may be configured to receive a section 215 of the pipe 210. Orifice block 230 may include one or more attachment members that holds pipe 210 in a region of the orifice block 230. That region of the orifice block may include components that align with openings in the outer wall of pipe 210 to enable a sample of gas to be extracted from pipe 210 and/or a sample of gas to be returned to pipe 210 after analysis. Unit 210 alternatively or additionally may be configured to position sensors adjacent openings in pipe 210 so as to measure flow of the landfill gas through the pipe 210, properties of the gas flow, such as pressure, or characteristics of the gas within pipe 210, such as its composition or percentage or amount of one or more constituent gasses, such as methane, oxygen, carbon dioxide, and/or hydrogen sulfide, for example.

Figure 3:
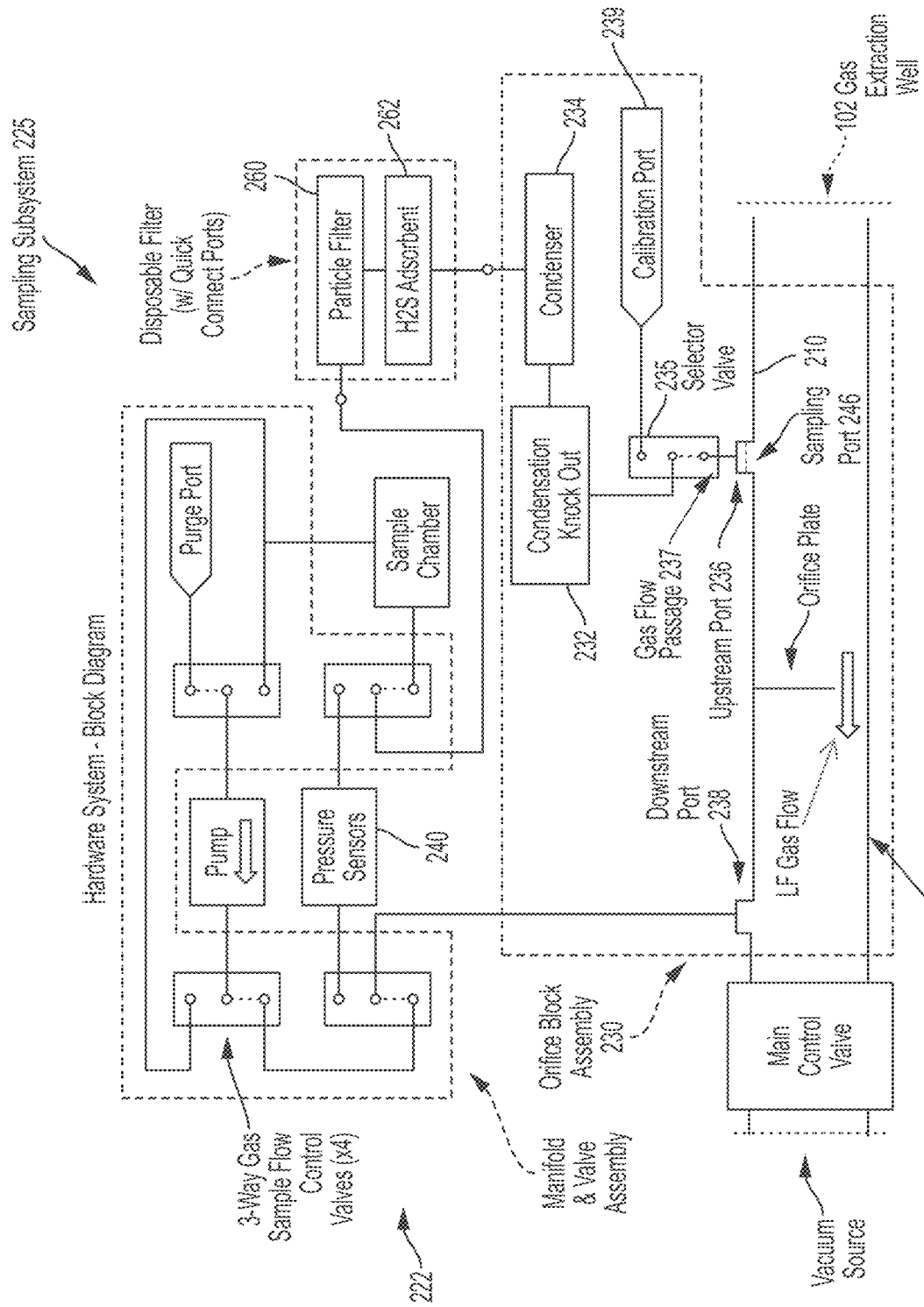
FIG. 3 is a block diagram illustrating an exemplary enclosure according to some embodiments.

FIG. 3 illustrates an exemplary collection of components that may be within enclosure 220, according to some embodiments. In some embodiments, the orifice block 230 may include a gas inlet port 236 and a gas outlet port 238. Additionally, the orifice block 230 may include a region configured to receive the section 215 of the pipe 210 having a gas sampling port 246.

According to some embodiments, the orifice block 230 may include an attachment member that mechanically couples the orifice block 230 to the section 215 of the pipe 210 with the gas inlet port 236 of the orifice block 230 in gas flow communication with the gas sampling port 246 of the section 215 of the pipe 210.

According to some embodiments, the orifice block 230 may include a gas flow passage 237 from the gas inlet port 236 to the gas outlet port 238. One or more components may be connected in that gas flow passage 237 to condition gas before it is exposed to a sensor. Such conditioning may reduce damage to the sensor from the harmful characteristics of the LFG. For example, the gas flow passage 237 may have at least one fluid knock-out 232, which may aid in removing moisture from the LFG. Alternatively or additionally, the gas flow passage 237 may include one or more filters and/or may contact components to cool the gas.

According to some embodiments, the unit 200 may include at least one sensor device 240 disposed in a region 222 of the enclosure. The at least one sensor device 240 may be a gas sensor. Additionally, the unit 200 may include thermal insulation 250 positioned to retain heat from the section 215 of the pipe 210 in the region 222 of the enclosure 220. Such insulation may aid in low temperature operation, such as may be expected in winter conditions. Heat from the gas may be used alone or in combination with other heat sources to ensure that components continue to operate in cold conditions. A sampling unit or an actuator, for example, might cease to operate or cease to operate accurately if condensation formed in the unit and then froze. Other components, such as a battery, might simply be degraded by cold temperatures, such as temperatures below 32 degrees Fahrenheit, and or all of these components may be heated as described herein.

According to some embodiments, the at least one sensor device 240 may be coupled to the section 215 of the pipe 210 through the gas sampling port 246. Alternatively or additionally, the at least one sensor device 240 may be coupled to the gas outlet port 238.

As illustrated in FIG. 3, the unit 200 may include multiple valves or other actuators that may be controlled to allow or clock flow of gas through multiple passages. Those passages may, for example, be machined in a manifold block. Passages, and corresponding actuators, may be included in the manifold to implement functions as described herein. Those functions may include passing a gas sample into a sample chamber where measurements on the gas composition of gas flow may be made. Additionally, those actuators may be controlled to evacuate the sample gas from the sample chamber and/or inject purge gas into the sample chamber. The gas sample may be landfill gas or may be calibration gas. FIG. 3 illustrates an exemplary configuration that supports these functions. However, other configurations may be used.

Filtration Elements and Methods

To promote the longevity and reliability of sensing devices interfacing with the LFG stream, some embodiments may employ one or more filtration elements and methods to reduce the impact of potentially harmful characteristics of the LFG stream. The filtration elements may be coupled in the gas flow passage inside unit 200, or in any other suitable way. Furthermore, the filtration elements and methods may be implemented in novel ways to make some embodiments as small, compact, and integrated while still improving filtration efficacy. Certain design considerations described herein may reduce the number of tubing connections, improve reliability of seals, and reduce manufacturing effort. The following details ways this may be designed and implemented:

Integrated Water Knock-Outs

In some embodiments, the filtration system may contain an integrated knock-out to separate fluids in the gas stream, such as condensate, from the gas being sampled. The knock-out (232, for example) may be integrated into specially designed hardware, such as the orifice block, or a separate unit in line with the sense and measurement system.

According to some embodiments, the at least one fluid knock-out 232 may be configured to separate at least one fluid from the landfill gas. Additionally, the fluid knock-out 232 may include a vessel having a first cross-sectional area larger than a second cross-sectional area of the gas inlet port 236 and/or a third cross-sectional area of the gas outlet port 238, as shown in FIGS. 4-7.

For example, in some embodiments, the knock-out may be implemented by having an inlet port or fluid path with a smaller cross-sectional area feed into a vessel of larger cross-sectional area or volume. Upon aspirating a gas/vapor sample with the undesirable liquid (for example, condensate) present, the liquid will be retained in the bottom of the vessel while the gas/vapor may continue through the outlet path towards the top of the vessel.

In some embodiments, this knock-out may be implemented by milling or boring a cavity into a block that serves as a support for other elements in unit 200 (for example, the orifice block) to connect internal fluid paths with a smaller cross-sectional area or volume, such that the cavity provides a knock-out volume for aspirated gas/vapor and liquid to be separated allowing only gas or vapor to proceed to the outlet of the cavity.

In some embodiments, the cross-sectional area or volume of the knock-out may be selected through calculations or empirical determination of characteristics such as, but not limited to, the velocity of the aspirated fluid, the viscosity of the aspirated fluid, the geometric characteristics of the inlet path (such as diameter, cross-sectional area or volume), the geometric characteristics of the outlet path, fluid adhesion to the wetted materials, flow duration or total aspirated volume in a sample cycle.

Figure 4:
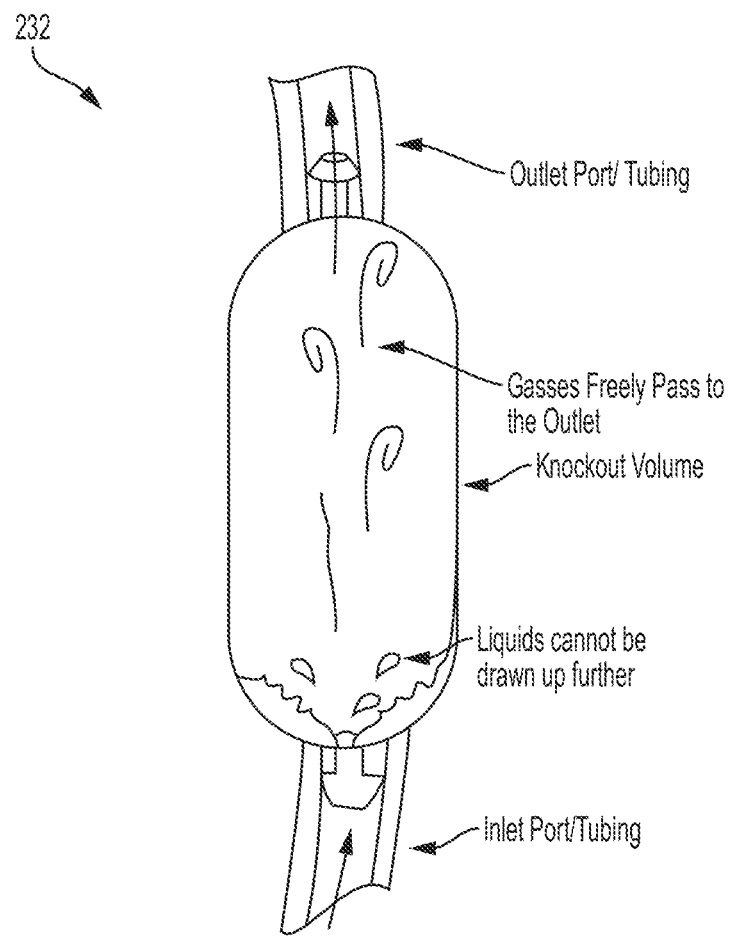
FIGS. 4-6 are sketches illustrating different fluid knockouts, according to some embodiments.
Figure 5:
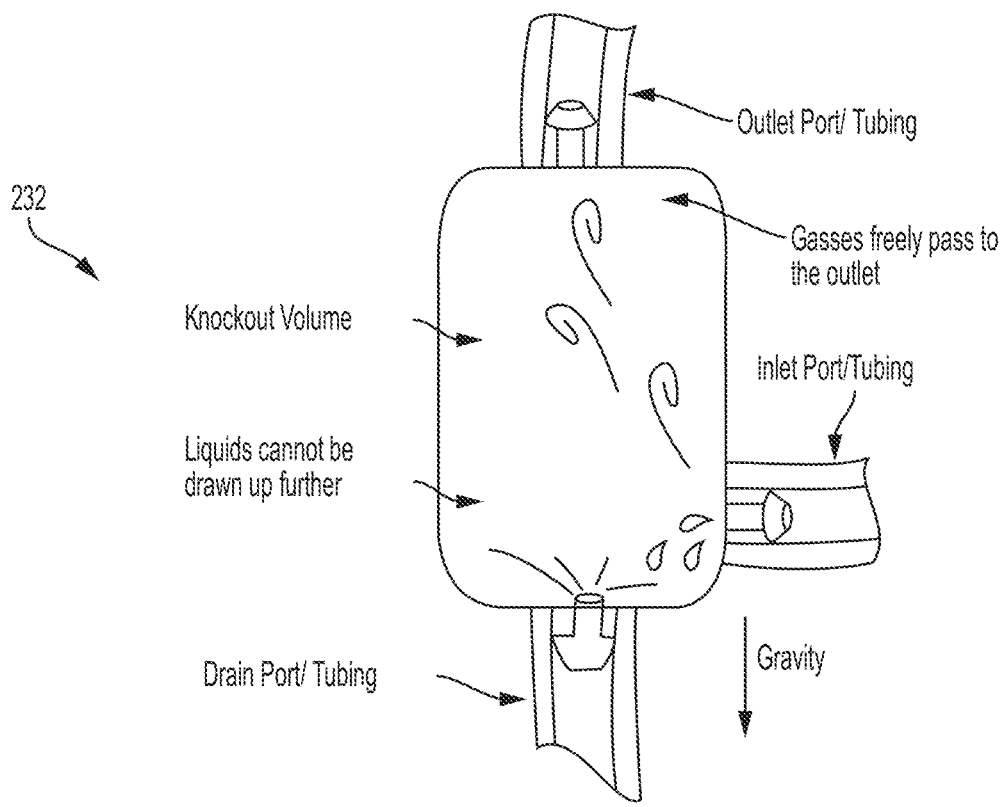

According to some embodiments, the at least one fluid knock-out 232 comprises a drain port configured to drain the at least one fluid. In some embodiments, the gas outlet port may include a drain port configured to drain the at least one fluid, as shown in FIG. 4. Alternatively, the drain port may be separate from the gas outlet port 238, as shown in FIG. 5. According to some embodiments, the at least one fluid knock-out 232 (or the unit 200) may include at least one valve configured to open and close the drain port.

For example, in some embodiments, the liquid separated by the knock-out may drain through the same port through which fluid was drawn, or a separate port dedicated to draining liquid that may be toggled using a dedicated valve.

In some embodiments, this liquid may be actively expelled from the knock-out by reversing flow direction through the vessel—such that the sample inlet becomes the purge outlet—or by the use of a dedicated pump or valve system designed to extract or expel fluid from the vessel.

In some embodiments, this liquid may be passively expelled through the use of gravity and the knock-out may employ valves to toggle drainage ports.

In some embodiments, the knock-out may employ materials to alter the fluid path (such as porous media, foam, sintered metal, pebbles, or silica beads) or geometry features such as zig-zags, elbows, or other tortuous paths, to impede the travel of liquids from the inlet to the outlet.

Figure 8:
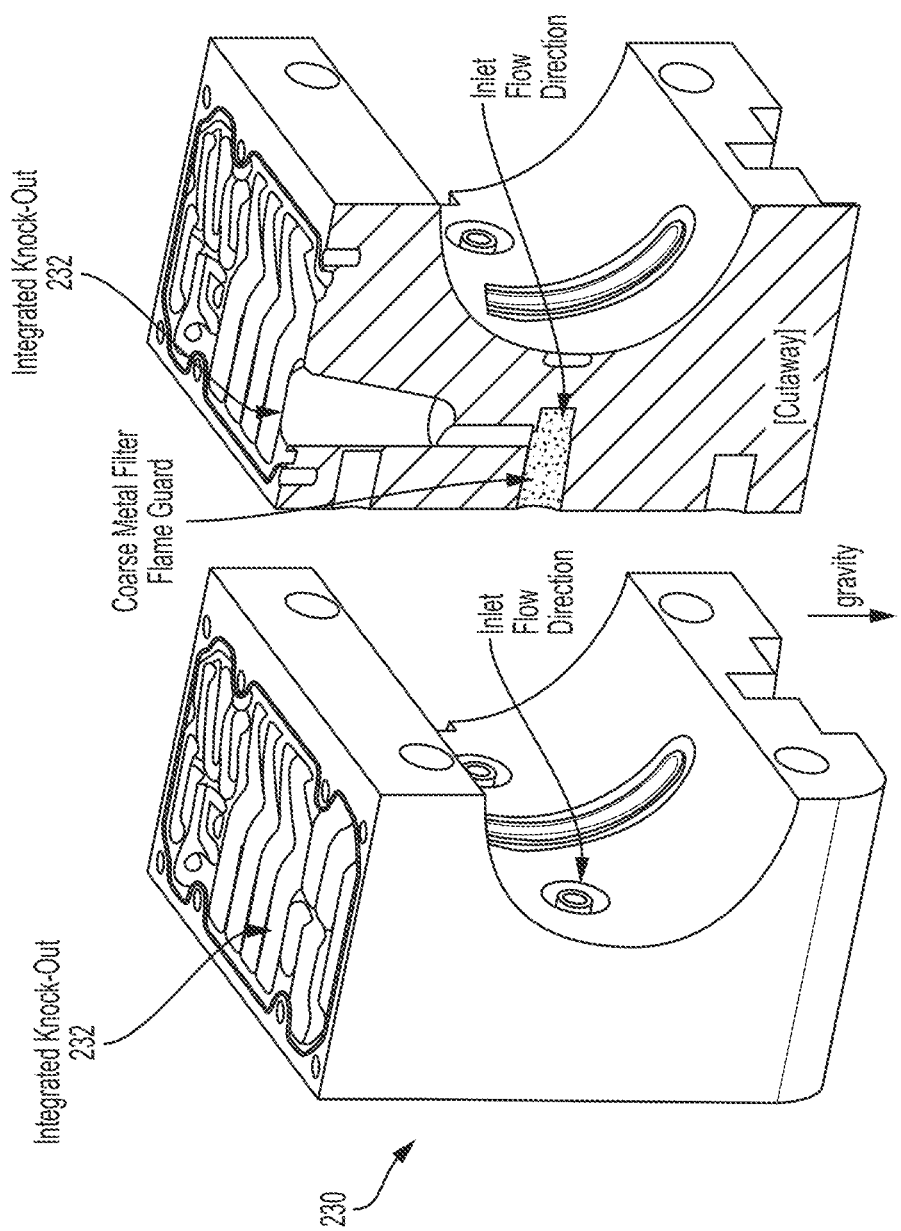
FIG. 8 is a diagram illustrating an orifice block, according to some embodiments.
Figure 9:
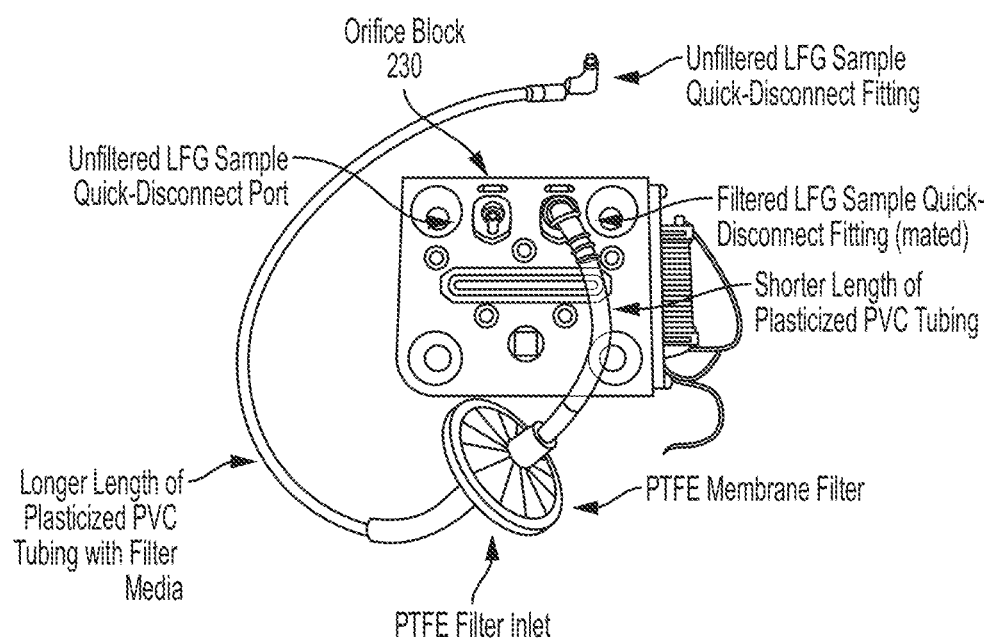
FIG. 9 is a diagram illustrating an orifice block and a filter, according to some embodiments.

In some embodiments, the knock-out may be preceded by or include a metal mesh or wool (as shown in FIG. 8), such as stainless steel wool, that provides both coarse particulate filtration as well as a flame barrier.

Figure 6:
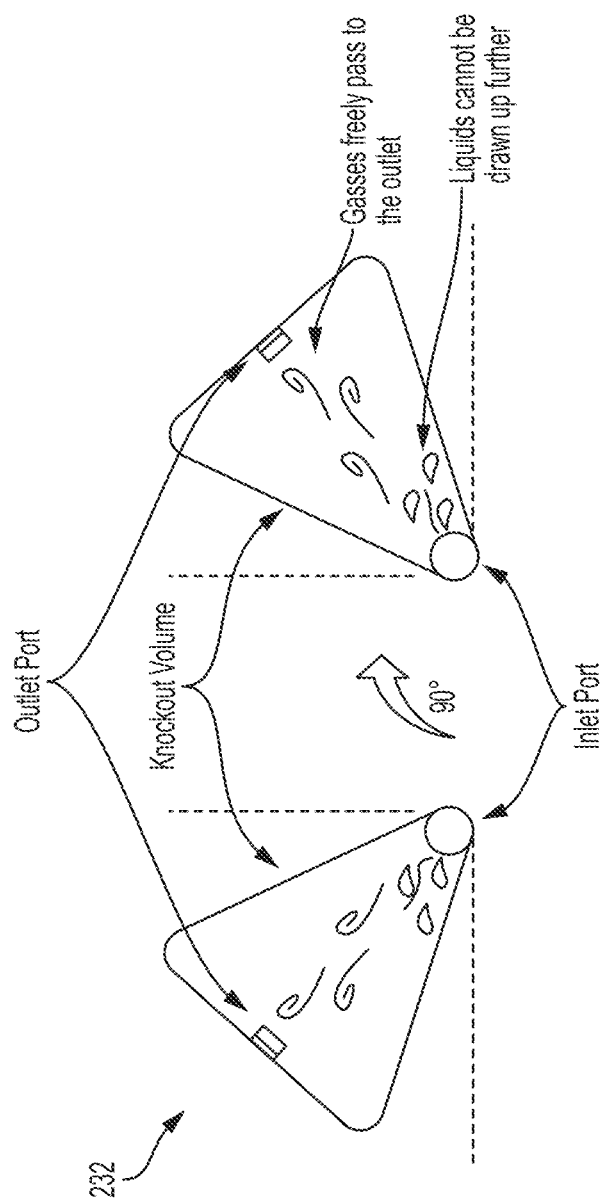

FIG. 6 illustrates multiple orientations the at least one fluid knock-out 232 may have. For example, the at least one fluid knock-out 232 may be arranged such that a line between the gas inlet port 236 and the gas outlet port 238 is about 60 degrees from vertical. In some embodiments, the knock-out may be designed to function equally well in two different orientations that are 90 degrees rotated from each other, such as is shown in FIG. 6. This design may be useful when the fluid system may need to be mounted in a vertical or horizontal position with as little effect on performance as possible.

Active Condensing Element

In some embodiments, an active condensing element may be employed to remove undesirable water vapor from the aspirated gas sample as an alternative to or in addition to traditional methods including, but not limited to, using consumable desiccant media.

In some embodiments, this active condensing element (234, for example) may include a chilled volume through which the aspirated gas is passed to decrease the gas temperature below the dew point, decreasing moisture content from the inlet of the element to the outlet as water condenses out along the way.

According to some embodiments, the enclosure 220 may include at least one active condensing element, such as a thermoelectric condenser 234. The thermoelectric condenser 234 may separate at least one undesired element (for example, moisture) from the landfill gas.

According to some embodiments, a gas flow passage of the orifice block 230 may pass adjacent to and in thermal contact with the thermoelectric condenser 234.

Figure 7:
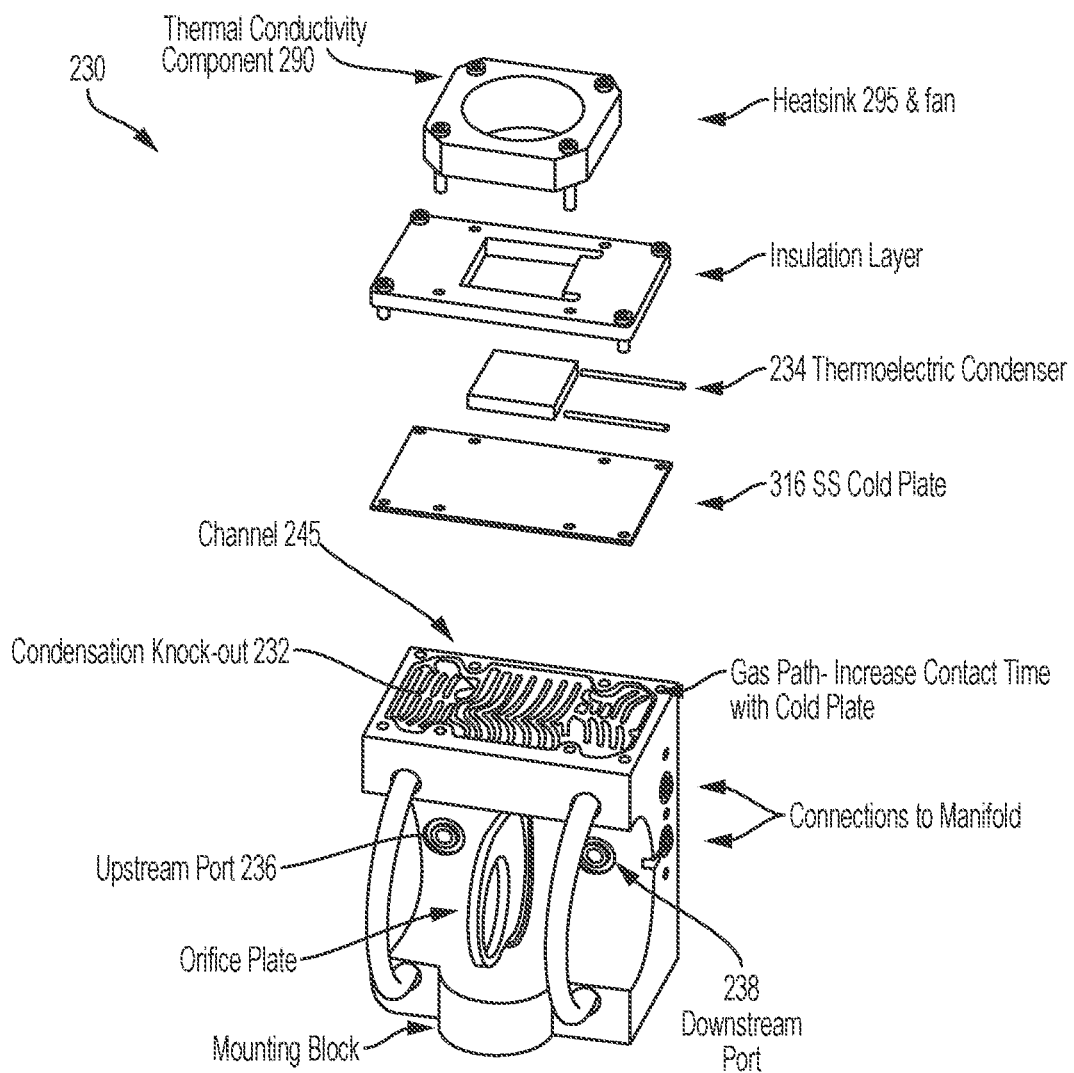
FIG. 7 is an exploded view of an orifice block and heat management components, according to some embodiments.

According to some embodiments, the thermoelectric condenser 234 may include at least one chilled surface. Alternatively, the thermoelectric condenser 234 may be covered by at least one chilled plate. In some embodiments, the thermoelectric condenser 234 may comprise at least one channel 245 at a surface of a block, such as the orifice block 230. Additionally, the at least one channel 245 may direct the landfill gas across the at least one chilled plate. As shown in FIG. 7, for example, a thermoelectric element may be mounted on a cold plate that serves as a cover on a twisting gas flow passage on an upper surface of the orifice block 230. The cold plate may retain the gas in the gas flow path, and the thermoelectric element may be in thermal contact with the gas through the cold plate. The knockout 232 may have an opening into that upper surface such that condensed moisture may be removed through the knockout 232. The twisting gas flow path may increase contact time between the gas and the cold plate.

For example, in some embodiments, the chilled volume may be implemented by channels integrally formed with the orifice block 230, such as during a molding operation.

Alternatively, the active condensing element may include a chilled surface across which the aspirated gas is passed to decrease the gas temperature below the dew point, decreasing moisture content from the inlet of the element to the outlet as water condenses out along the way. In some embodiments, this chilled surface may be implemented as a face or faces of a physical block (for example, the orifice block 230) or manifold that also houses other gas paths or filtration elements. Alternatively, this chilled surface may be attached to a face or faces of a physical block (for example, the orifice block 230) or manifold containing other gas paths or filtration elements.

In some embodiments, this chilled surface may be made from a thermally conductive metal sheet that may be corrosion resistant (for example, 316 stainless steel). In some embodiments, this metal sheet may be chosen to have specific properties including, but not limited to, good thermal conduction and chemical resistance. Additionally, this metal sheet may be designed to have a thickness and area, the combination of which comprising a characteristic volume, which may be selected through calculation or empirical determination to reduce thermal capacitance as much as possible and increase thermal conduction as much as possible to improve efficiency and speed of chilling.

In some embodiments, this metal sheet may be structurally reinforced with a more rigid and thermally insulating material that provides a flat compressing surface and insulation between the chilled surface and ambient.

In some embodiments, the face that this chilled surface is affixed to may contain features (like channels) such as zig-zags, elbows, turns, meanders, or other tortuous routes that direct the gas across the chilled surface in order to optimize the contact time between the gas and the chilled surface.

In some embodiments, the route or routes on this face may be designed using calculations or empirical determination to maximize chilled surface area exposed to the gas, minimize the pressure drop from inlet to outlet, maximize turbulence or circulation across the chilled surface, create pressure changes that promote condensation, minimize traps where condensed liquid might accumulate, ensure manufacturability, and otherwise maximize efficiency of humidity removal.

In some embodiments, the route or routes on this face may be designed to promote purging of condensation from the element when the flow direction is reversed.

In some embodiments, the chilled surface may be cooled through means of forced convection (for example, through the use of a fan), passive thermal conduction or convection (for example, by heat sinking the surface to a colder environment or ambient temperature), or through a (active) heat pump, such as a solid-state device (for example, thermoelectric) or electromechanical system (for example, compressor-based refrigeration).

In some embodiments, a control system may be employed to selectively cool the chilled surface at a specific time such as before sample aspiration to pre-cool the surface or during sample aspiration, and remain off at other times.

In some embodiments, this control system may be open-loop, for instance operating for a preset amount of time, at a preset duty cycle or at a preset power level.

In some embodiments, this preset time may be determined through calculation or empirical determination to optimize across most condensation needs given a range of sample humidity constraints and a specified power budget.

In some embodiments, this control system may be closed-loop, using feedback to regulate a control signal to optimize for goals such as minimal power consumption or maximum filter efficacy. For instance, if the ambient temperature and therefore condensing element temperature is already much colder than the sample gas, the chiller may not need to run as long or as high power to achieve the optimal condensing effect.

In some embodiments, this feedback may be from one or many sensors including, but not limited to, sensors in the LFG path or sample path measuring gas sample humidity, sensors in the LFG path or sample path measuring temperature of the gas, sensors bonded to the heat pump or chilled surface measuring instantaneous output temperature or temperature sensors measuring ambient or external environment temperatures.

In some embodiments, condensate that accumulates in or on the condensing element may drain passively from gravity or be actively purged by reversing the direction of gas flow through the system.

In some embodiments, the heat pump used to chill the element may also be run in reverse to instead heat the condensing element, assisting in the vaporization and removal of accumulated condensate and drying the condensing surfaces before the next sample cycle.

In some embodiments, the thermoelectric element may be driven with a single MOSFET that closes the circuit across a battery and the thermoelectric, or it may be driven by a full bridge (h-bridge) that allows the reversal of the polarity on the thermoelectric. For instance, the bridge may drive the thermoelectric normally to cool and then in reverse to heat.

Thermoelectric Active Condensing Element Manufacturing Process

In one embodiment, the active condensing element may be constructed from the following:

An indirect gas flow path with inlet and outlet routed on a face of the orifice block a dovetail or other undercut on this same face meant to hold captive an O-ring a stamped, cut, waterjet and/or drilled sheet of 316 stainless steel to serve as the chilled surface a corresponding plate or 'lid' of acetal to provide a backing to the relatively flimsier sheet of 316 stainless steel an O-ring on this same face of the orifice block to provide a gas-tight seal between the stainless sheet and the tortuous gas path; this plate contains provisions/cutouts to accommodate for the thermoelectric volume and the wires that connect to the thermoelectric threaded inserts on this same face of the orifice block screws (with nylon washers) that drive into the inserts to compress the acetal against the stainless sheet against the O-ring to make a gas-tight seal a thermoelectric element, such as a Peltier device, with the 'cold side' (the side of the thermoelectric that chills when energized with the marked polarity) thermally bonded to the stainless steel sheet (requiring a cutout in the acetal plate)

a heat sink with fan thermally bonded to the 'hot side' (the side of the thermoelectric that heats when energized with the marked polarity)

laser-cut polyamide used to mask thermal compound used in bonding to the thermoelectric; the polyamide sheet is affixed to the desired surface (stainless sheet or heatsink) and the mask is laser-cut in-situ In this embodiment, the process to assemble the condensing element may be as follows:
1. install threaded inserts on face of orifice block
2. insert O-ring into corresponding undercut route
3. mask the stainless steel cold plate, in this case using a polyamide adhesive film where the negative was laser-cut in-situ, by peeling out the negative
4. apply thermal compound (epoxy or grease) to plate and squeegee until it is uniformly covered
5. remove the remaining polyamide mask
6. place the acetal plate onto the cold plate, aligning clearance holes
7. place the thermoelectric cold-side down on the thermal pasted section of the cold plate
8. place the cold plate onto the corresponding orifice block face and align the screw clearance holes with the inserts
9. apply thread-lock to the screws (with nylon washers)
10. mask heatsink using identical method to cold plate and peel off the negative
11. apply thermal compound to heatsink and squeegee until it is uniformly covered
12. remove the remaining polyamide mask
13. place heatsink on the exposed thermoelectric face, centering the thermal paste over the thermoelectric and aligning screw clearance holes with corresponding inserts
14. insert all screws (with nylon washers), compressing thermal and sealing surfaces and completing assembly In some embodiments, the mechanism for compressing the sealing and thermal surfaces may be something other than screws, including springs, latches, or clasps. In some embodiments, compression may be unnecessary after assembly when instead replaced with thermal epoxy is used for the thermal connections or if a permanent sealant (solvent, RTV, epoxy, etc.) is used for the gas-tight sealing surfaces.

In some embodiments, the gas-tight seal may be made using a flat gasket that is compressed between the stainless plate and the face of the orifice block.

H2S Adsorbent Media Filter with Particulate and Liquid Barrier

According to some embodiments, the unit 200 may include a filter 260 for at least one of a particulate and/or a corrosive gas. The filter 260 may be disposed outside the orifice block 230, as shown in FIG. 3. Alternatively, the filter 260 may be disposed within the orifice block 230.

According to some embodiments, the unit 200 may include at least one consumable medium 262. In some embodiments, the at least one consumable medium 262 may be used to scrub at least one contaminant from the landfill gas. Additionally, the at least one consumable medium 262 may include at least one of an adsorbent activated charcoal, hydrogen sulfide, and a disposable cartridge.

For example, in some embodiments, consumable media (for instance, an adsorbent activated charcoal or an iron-based compound) may be used to scrub the hydrogen sulfide or other contaminants (H2S) from the sample gas.

According to some embodiments, the filter 260 may include at least one fine particulate filter located downstream of the at least one consumable medium 262. For example, in some embodiments, this media may be retained using porous foam that also acts as a coarse filter, allowing gas to pass across it but preventing the media from proliferating beyond the filter ports. In some embodiments, this foam may be chosen to be chemically inert or resistant to H2S.

According to some embodiments, this media may be packaged in a vessel with an inlet and an outlet port. In some embodiments, this vessel may be designed for regular disassembly and emptied so that spent media can be replaced with fresh media (i.e. a "refillable" media cartridge). Additionally, in some embodiments, this vessel may be designed to be disposable so that an entire spent filter assembly may be economically replaced with a fresh filter.

In some embodiments, this vessel may be designed or chosen to be as compact as possible. For instance, the vessel may be a length of flexible tubing that can be wound into a compact form factor while maintaining a desirable volume and flow path length.

In some embodiments, the length and cross sectional area of the fluid path may be designed using calculations or empirical determination to apply optimizations including, but not limited to, maximizing gas sample residence time on the media and minimizing pressure drop across the media.

In some embodiments, a fine particulate filter, such as a PTFE membrane filter, may be located downstream of the consumable media to filter dust in the LFG sample as well as dust from the media.

In some embodiments, the particulate filter, such as a PTFE membrane filter, may also serve as a liquid barrier to prevent any liquid that managed to defeat previous mitigation strategies from propagating further through the sampling system In embodiments, this filter shall be designed for easy service and replacement. In some embodiments, the system may be designed to determine when a filter, such as an $H_2S$ scrubber, needs replacement or to project when such a filter will require replacement. Such a determination or projection may be based on on-going measurements of the filter's effectiveness.

Effectiveness may be determined, for example, from upstream and downstream measurements of the component being removed by the filter. For an H2S scrubber, for example, the effectiveness may be determined by the ratio of upstream to downstream amount of H2S measured. In a system as described herein in which any of multiple locations in the sampling system may be coupled to a sensor chamber, such a measurement may be made by coupling a downstream location to the sample chamber and then coupling the upstream location. The measured ratio may be compared to the ratio expected for a properly operating filter. For example, a properly operating filter may remove at least 50% of the component.

A comparison of upstream to downstream amounts of the component may alternatively or additionally be based on an amount of the component removed by the filter rather than a ratio. For example a properly operating filter may remove at least 500 ppm of the gas. Alternatively or additionally, the amount of the compound removed may be based both on concentration and flow rate, yielding an amount of the component removed from the gas per second, which can be compared to a rated value for a properly working filter.

These or any other suitable upstream to downstream comparison may be compared to rated values for a properly operating filter. If the comparison indicates effectiveness below the rated value, a message may be sent by the system controller 275, alerting an operator to change the filter. Alternatively or additionally, the effectiveness may be tracked over time, by the controller 275 of the sampling subsystem 225 or other computerized device coupled to the controller 275. The rate of change in effectiveness may be used to predict a time when the effectiveness will be below the rated value for a properly operating filter, allowing an operator to plan for maintenance.

Manufacturing Process

In one embodiment, the consumable filter may be constructed from the following:
- a longer length (around 18 inches) of plasticized PVC tubing that provides the gas path through the filter media
- a quick-disconnect fitting (for easy removal) that mates with the unfiltered LFG sample port on the orifice block and inserts into the longer length of tubing
- adsorbent filter media loaded into this longer length of tubing
- porous polyamide foam plugs, inserted into this longer length of tubing after filter media is loaded
- a PTFE membrane filter with barb fittings on both sides, with the inlet port inserted into the longer length of tubing
- a shorter length (about 4 inches) of plasticized PVC tubing that provides the gas path from the outlet of the PTFE membrane filter back into the orifice block
- a quick-disconnect fitting that mates with the filtered LFG sample inlet port on the orifice block and inserts into the shorter length of tubing In this embodiment, the process to assemble the consumable filter:

In some embodiments, the PTFE filter may also include quick-disconnect fitting connections to the tubing, allowing it to be treated as a separate consumable.

In some embodiments, the consumable filter assembly may instead be designed as a disposable cartridge with PTFE membrane, filter media and porous foam entirely integrated.

In some embodiments, this disposable cartridge may be made from thermoformed plastic, such as PETG, with a bonded film sealing across the top.

In some embodiments, this disposable cartridge may be manufactured in such a way that the film, otherwise entirely sealing the cartridge, can be punctured at the inlet and outlet ports through a mating clasp on the device assembly.

In some embodiments, this disposable cartridge may be manufactured in such a way that the puncture location has features designed to create a gas-tight seal with the mating clasp on the device assembly.

Orientation and Design of Fluid Paths to Minimize Fluid Accumulation

In some embodiments, the orientation and direction of fluid paths, including but not limited to, routed or drilled channels, tubing used to convey gas flow or pressure, or pipes and pipe nipples may be constructed or arranged in such a way that the lowest point in the path does not create a trap, s-bend, or u-bend where liquid can accumulate.

In some embodiments, the orientation and direction of these fluid paths may be designed such that the lowest points contain a port, drain, or outlet through which any accumulated liquids may naturally drain or be purged.

In some embodiments, the orientation and direction of fluid or pressure ports may be designed in such a way to preferentially point towards or away from, but not normal to, the direction of gravity. As can be seen for example, in FIGS. 7 and 8, a unit 200 may contain an orifice block 230 that has a region configured to receive a section of pipe 210. That region may fix the orientation of the orifice block 230, and the other components of unit 200, relative to the pipe 210. By configuring the orifice block 230 for attachment to a horizontal or vertical pipe, the orientation of components in unit 200 with respect to gravity may be established.

In some embodiments, the location of these ports on any chambers, vessels, or volumes may be preferentially located at the top and/or bottom of the chamber, vessel, or volume with at least one port on the bottom so that any accumulated fluid may purge through the bottom port.

In some embodiments, these chambers, vessels or volumes may preferentially have inlet and outlet ports on opposite sides to promote complete exchange of the fluid in the vessel during purge or sample cycles.

In some embodiments, the fluid paths, chambers, vessels, or volumes may include additional ports or routes located at the lowest point in the path, chamber, vessel, or volume—especially in cases where it may not be possible to locate the inlet or outlet ports at the lowest point—to facilitate draining of accumulated fluids.

In some embodiments, it may be advantageous to orient flow paths at a 45 degree angle such that orienting the device horizontally or vertically still allows for adequate performance.

In some embodiments, fluid handling hardware including, but not limited to, valves and pumps, may be installed in an orientation to ensure that the internal geometry of does create a low point that encourages liquid accumulation or inhibits liquid evacuation. For instance, a valve may be mounted to a manifold with ports facing downward towards gravity, allowing liquids to naturally drain, as shown in FIG. 10. Likewise, a pump may be installed onto a manifold such that the inlet and outlet ports face downward, allowing liquids to naturally drain.

In some embodiments, a coalescing element may be added to all gas inlets into this gas sampling system. In some embodiments, this coalescing element may be a metal mesh or wool, such as stainless steel wool. In some embodiments, this coalescing element may also function as a coarse particulate filter, a flame barrier, or a condensing element if it is cooler than the gas passing through it.

Techniques for Robust Measurements

Calibration Devices and Methods

Figure 11:
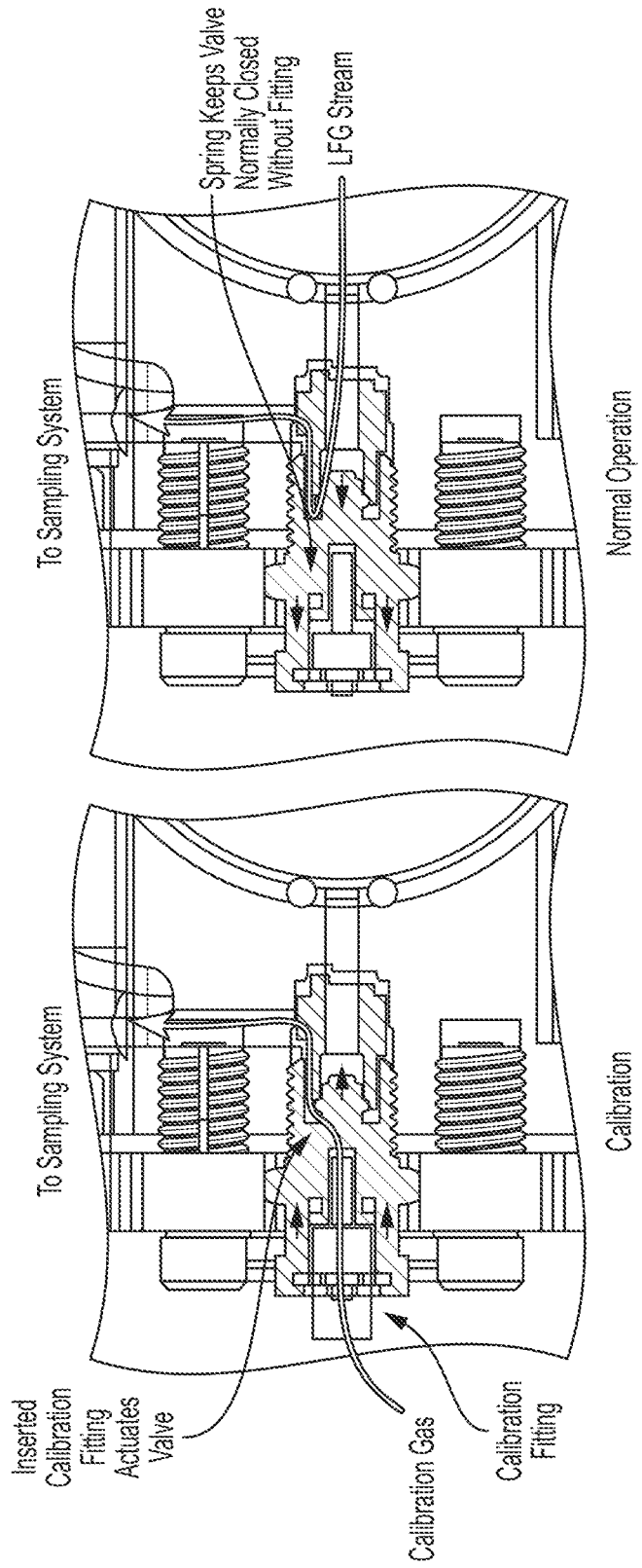
FIG. 11 is a diagram illustrating a calibration port, according to some embodiments.

According to some embodiments, the unit 200 may include at least one calibration port 239, as shown in FIGS. 3 and 11. Some embodiments may employ a calibration port 239 configured for connection to a source of a gas of known composition and for aspirating such a gas of a known composition for sensor calibration. For example, the calibration port 239 may be used to aspirate at least one gas of a known composition for calibration of the at least one sensor device 240. In another example, calibration port 239 may be used to aspirate outside air for calibration of the at least one sensor device 240. In such an embodiment, calibration may be based on measuring ambient oxygen. As the amount of ambient oxygen is readily constant, calibration with outside air as the calibration gas can provide a simple mechanism to frequently calibrate an oxygen sensor.

Moreover, in some embodiments, sensors that operate on the same principle as an oxygen sensor may be calibrated based on the oxygen sensor calibration. For example, oxygen, methane and carbon dioxide may all be measured with a non-dispersive IR sensor. Sensors for methane and carbon dioxide may require the same calibration factors as an oxygen sensor, which may be determined based on the calibration measurements on the oxygen sensor. One or more calibration ports may be coupled to one or more sources of gas of known composition. In some embodiments, that gas of known composition may be air. In this embodiment, the calibration port may be exposed to ambient air. In other embodiments, the one or more sources of gas of known composition may be gas canisters, filled with calibration gas of known composition or other suitable mechanism to provide calibration gas. In these embodiments, the at least one source gas of known composition may be a mixture of $CO_2$ and $CH_4$. In yet other embodiments, the apparatus may be configured to couple gasses of two or, in some embodiments, more sources of calibration gas. Those sources may include a source of air and a source of gas that is a mixture of at least $CO_2$ and $CH_4$. As a specific example, a calibration gas may comprise 35% $CO_2$, 50% $CH_4$, and 15% $N_2$. Here, percentages may be determined in any suitable way, including by volume, mass, molar fraction or partial pressure. As another specific example of a calibration gas that might be used, the calibration gas may be a calibration gas used in the industry for calibration of handheld devices, consisting essentially of 35% $CO_2$, 50% methane, and 15% $N_2$, with minor deviations as a result of impurities In some embodiments, this calibration port 239 may be installed in the gas sampling path so the calibration gas may pass through the same fluid system, including filters, valves, and knock-out vessels, as the gas sample from the LFG stream.

In some embodiments, this calibration port 239 may be used in conjunction with a valve 235 that diverts the sample path from the LFG stream to the calibration port. The valve 235 may be connected between the calibration port 239 and a sensor, so as to enable gas to flow from the calibration port to the sensor.

In some embodiments, this valve 235 may be integrated into the calibration port 239 such that insertion of a fitting into the calibration port 239 toggles the diversion of the sample path from the LFG stream to the calibration gas, and back again upon removal. Additionally, this valve 235 may be toggled through an electronic device that may be signaled by a command on a user interface or by the detection of a fitting connected to the calibration port 239.

In some embodiments, this valve 235 may be toggled through mechanical action, such that insertion of a fitting into the calibration port 239 mechanically actuates the integrated valve.

In some embodiments, this calibration port 239 may be installed in a separate location in the gas sampling path, possibly bypassing some or all of the paths used to sample gas from the LFG stream.

Some embodiments may employ a calibration method that requires the use of a comparable gas path in instances where diversion of the gas sample stream may not be applicable or practical. For instance, even though calibration gas is nominally clean, it may still be advantageous to pass the gas through an characteristic device, such as but not limited to an external filter, vessel or length of tubing that may emulate the same effects such as, but not limited to, mixing volume, fluid path length, chemical reactions or pressure drop as filters or volumes of the normal gas sampling path. This way, effects of the filter and sampling path may be accounted for in the calibration process.

Some embodiments may employ a calibration process comprising cycles that sample two or more gas mixtures of known and different composition to calculate linear (gain and offset) or nonlinear compensation for a single gas sensor.

Some embodiments may employ a calibration process comprising cycles that sample two or more gas mixtures of known, different and linearly independent composition or pure gasses to calculate linear (gain and offset) or nonlinear compensation for one or more gas composition sensors at a time.

In some embodiments, two gas mixtures of known composition may be measured to calculate the span or gain factor and zero offsets of one or more internal gas composition sensors, with the gain and offset applied to the measured value to yield a corrected value. For example, a gas with the known concentrations of 50% methane, 35% carbon dioxide and the remaining balance (15%) nitrogen by volume may be used to calculate the spans of a methane and/or carbon dioxide sensor and the zero offset of an oxygen sensor. Similarly, clean atmospheric air with the relatively consistent concentration of approximately 20.9% oxygen and nearly all of the remaining concentration as nitrogen may be used to calculate the zero offsets of a methane and/or carbon dioxide sensor and the span of an oxygen sensor.

In some embodiments, the two or more gas mixtures of known composition may have non-zero concentrations for all gases being measured as long as the different gas mixtures comprise a linear combination of concentrations that occupies the basis vectors necessary to calculate a calibration for each sensor.

In some embodiments, it may be necessary or desirable to calibrate the gas sensor for each constituent gas individually with one gas mixture at a time to reduce cross sensitivity from other gasses in the calibration mixture.

In some embodiments, in an alternate sensor configuration sensors may be calibrated simultaneously to directly calculate and compensate for cross sensitivity across gasses in the measurement. For instance, calibration might use a mixture with concentrations of each gas, possibly using concentrations typical of those found in an LFG stream.

Some embodiments may employ a calibration process comprising cycles that sample two or more gas mixtures of known and different composition at two or more absolute pressures to calculate linear (gain and offset) or nonlinear compensation to correct for effects of pressure on the measurement.

In some embodiments, the sample pump that draws in the gas sample (and calibration sample) may be throttled to create these conditions of different absolute pressure and flow within the gas sample chamber that houses the gas composition sensors.

In some embodiments, this gas sample chamber pressure may be measured by one or more pressure sensors and may be used in the determination of the pressure compensation factors during a calibration.

In some embodiments, this gas sample chamber pressure reading may be used when applying pressure sensor compensation during normal measurement cycles to correct for the effects of pressure on the composition sensors.

Some embodiments may measure one or more pressures through the use of digital pressure transducers that may or may not have a zero offset.

In some embodiments, the output or value of these digital pressure transducers may be recorded during a calibration period of zero applied pressure and applied as an offset during an active measurement to eliminate offsets and improve sensor accuracy.

Measurement Hardware and Methods

Figure 12:
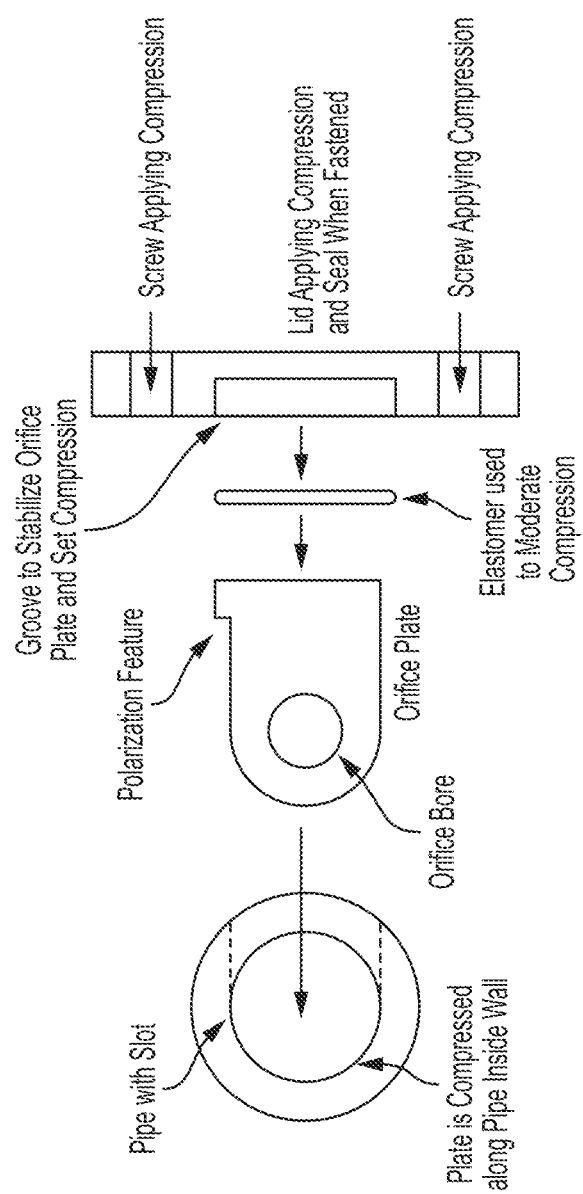
FIG. 12 is a sketch illustrating installation of an orifice plate, according to some embodiments.

In some embodiments, flow may be determined using a differential pressure device, such as but not limited to, an orifice plate, such as is shown in FIG. 12.

Figure 13:
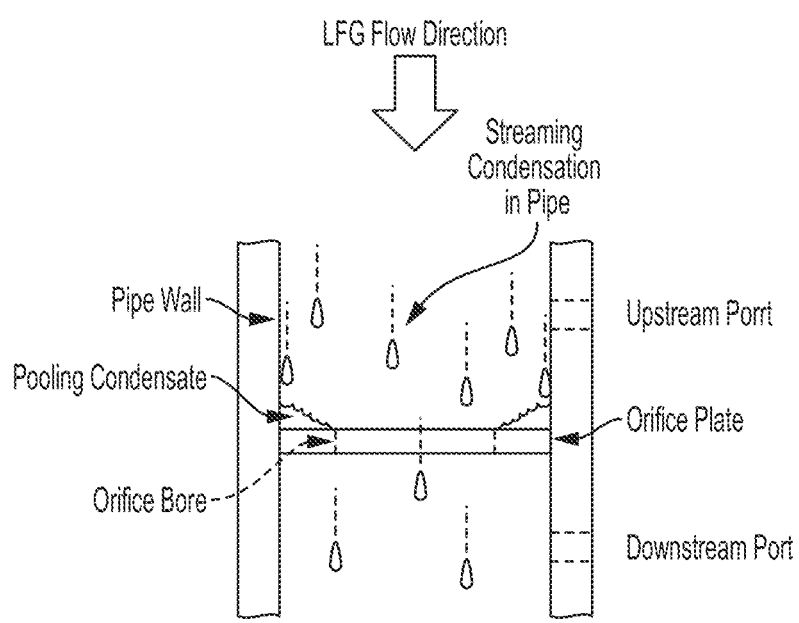
FIG. 13 is a diagram illustrating condensation in a pipe, according to some embodiments.

In some embodiments, the process to manufacture this orifice plate may be imperfect and cause repeatable manufacturing artifacts, such as a taper on the orifice bore (shown in FIGS. 12 and 13). For instance, the use of a laser cutter to create an orifice plate from acrylic stock may create a taper in the orifice bore cut.

In some embodiments, artifacts such as this taper may be mitigated by ensuring that the artifact is consistently reproduced across the entire batch and that the device is used in the same position each time.

In some embodiments, this orifice plate may utilize a polarizing feature such that the insertion of the orifice into some embodiments for the use in flow measurement is permitted to occur in only one way. For instance, adding a polarization tab to the orifice plate and the corresponding slot in which it is inserted would add this chirality.

In some embodiments, variations in the orifice plate or the pipe in which the orifice plate is inserted may make a perfect seal around the orifice plate and the inner pipe wall difficult to achieve. For instance, eccentricity caused in the CPVC pipe production process makes a perfect concentric and co-radial mate impossible.

In some embodiments, the orifice plate may be designed with a slight eccentricity that conforms to or otherwise minimized variation from the eccentricity of a particular batch or manufacturer of CPVC pipe.

In some embodiments, this orifice plate may be compressed against the pipe wall to assist in sealing between the orifice plate and the inner pipe wall (see FIG. 12, for example). As described herein, an orifice block 230 may include one or more attachment members. The attachment members, for example, may be U-shaped members that fit around the pipe 210. The ends of the members may pass through the orifice block 230 and may be threaded. By tightening a bolt, or otherwise drawing the attachment members toward the orifice block 230, the pipe may be compressed against the orifice block 230.

In some embodiments, the amount of compression may be calculated or otherwise empirically determined and then applied through the use of a specific groove, slot, pocket or other feature on a lid covering the slot in which the orifice plate is inserted, examples of which are shown in FIG. 12.

In some embodiments, this feature may also contain an elastomeric (shown in FIG. 12) or otherwise compressible material that can deform when compressed between the lid and the orifice plate to reduce the compression stress applied to the orifice plate.

Some embodiments may conduct a static pressure measurement of the LFG gas stream.

In some embodiments, this measurement may be conducted using a digital unidirectional pressure transducer that accurately measures positive pressures but not negative pressures, or vice versa.

In some embodiments, when installed on a well or extraction point with very low applied vacuum (such that the well static pressure is nearly at equilibrium with atmospheric pressure) this unidirectional measurement may be preferentially conducted using the port meant to convey pressure downstream of the orifice to ensure measurement of static pressures within the range of the device; given normal flow from a well through the device, the orifice plate will drop an amount of pressure with any flow through the LFG port ensuring the static pressure measured at the downstream port, relative to atmosphere, be of constant sign.

Some embodiments may be installed on an LFG stream with a high volume of flowing condensate, such as is shown in FIG. 13.

Some embodiments may be oriented in such a way that the flow through the orifice plate bore is normal to gravity such that flowing condensate may periodically accumulate on the cusp of the top or upstream of the orifice plate, as shown in FIG. 13.

Some embodiments oriented in this way may be preferentially designed to draw in the LFG gas sample through the downstream, or bottom, port to avoid pulling in liquid that may accumulate on the top, or upstream, side of the orifice plate.

Some embodiments may contain a control valve that regulates the impedance between a central vacuum system (available vacuum) and the LFG extraction point so as to correspondingly control flow from or applied vacuum to the extraction point.

Some embodiments may employ a digital pressure transducer to measure the vacuum on the downstream side of the control valve to provide an indication of the maximum system vacuum that could be applied to that extraction point.

In some embodiments, this available vacuum measurement may be combined with a pressure measurement upstream of the control valve to compute a differential pressure measurement across the valve.

In some embodiments, a differential pressure measurement across the valve may be combined with other information or measurements including, but not limited to, pressures, temperatures or rate of flow (from a flow measurement device in the same gas stream) to generate an impedance profile that correlates measured pressures (static and/or differential) and valve position to a corresponding valve impedance.

In some embodiments, this differential pressure measurement across the valve may be combined with other information or measurements including but not limited to, valve position (percentage open or closed), static pressure or temperature to infer the rate of flow of the LFG gas stream.

In some embodiments, this differential pressure measurement may be used as a feedback signal in a closed-loop control system that controls the valve position (percentage open or closed) in order to modulate the flow and extraction pressure.

In some embodiments, this available vacuum measurement may provide indications of system level behavior that may otherwise be difficult to determine. For instance, a drop in static pressure may be caused by a drop in system vacuum pressure instead of increase in flow or change in gas generation characteristics. Similarly, effects of a valve command on an individual well to the extraction system may be observed on deployed units with fluid connection to the extraction system without confounding measured pressure dynamics of the individual extraction points.

Some embodiments may employ one or more mitigation strategies to prevent condensate in the gas stream from interfering with the available vacuum measurement including, but not limited to, a knock-out or water trap, valves or pumps used to actively purge the measurement port, or a PTFE membrane filter.

In some embodiments, these mitigating features on the available vacuum port may be preceded by or include a metal mesh or wool, such as stainless steel wool, that provides both coarse particulate filtration as well as a flame barrier, as shown in FIG. 8. In some embodiments, this available vacuum knock-out may be passively or actively drained, such as is shown in FIGS. 4, 5, and 8.

In some embodiments, this knock-out and the entire fluid connection to the available vacuum transducer may be actively drained or purged by momentarily opening a connection from atmosphere to system vac through the available vacuum connection. For instance, under normal operation a normally closed valve may toggle open to allow a burst of atmosphere to be drawn through the available vacuum transducer connection by the system vacuum, pushing any accumulated condensate back through the port into the LFG stream.

Some embodiments may employ a port that connects internal fluid systems to atmosphere.

In some embodiments, this atmosphere port may be fluidly connected to a reference port on a pressure transducer to act as a reference for measurements such as static pressure or available vacuum.

In some embodiments, this atmosphere port may be used as an inlet so that clean air may be drawn in for use in purging one or more parts of the fluid handling system. For instance, a pump may actively pump this clean air through the sampling system to purge accumulated fluids. Likewise, a normally closed valve may open to allow the system vacuum to draw in clean air to similarly purge accumulated water back into the gas stream.

Some embodiments may employ a sample cycle that entirely purges the gas in the sampling system with clean air after each measurement. For instance, exposure of the gas sensor (or other hardware, such as pumps, valves, or filter elements) exposure to the potentially corrosive and dirty LFG sample may be limited by purging the gas sample from the sensor chamber and any fluid paths with clean air from this atmosphere port.

In some embodiments, this atmosphere port may employ one or more mitigation strategies to prevent aspiration of precipitation or condensation including, but not limited to, a knock-out or water trap, valves or pumps used to actively purge the measurement port, or a PTFE membrane filter.

In some embodiments, these mitigating features on the atmosphere port may be preceded by or include a metal mesh or wool, such as stainless steel wool, that provides both coarse particulate filtration as well as a flame barrier.

In some embodiments, a coarse mesh, foam, or wool that may or may not be the same as this coarse particulate filter or flame barrier may be employed to prevent spider, insects, dust, plants, or miscellaneous detritus ingress.

Designs for Surviving Sub-Freezing Weather

Figure 14:
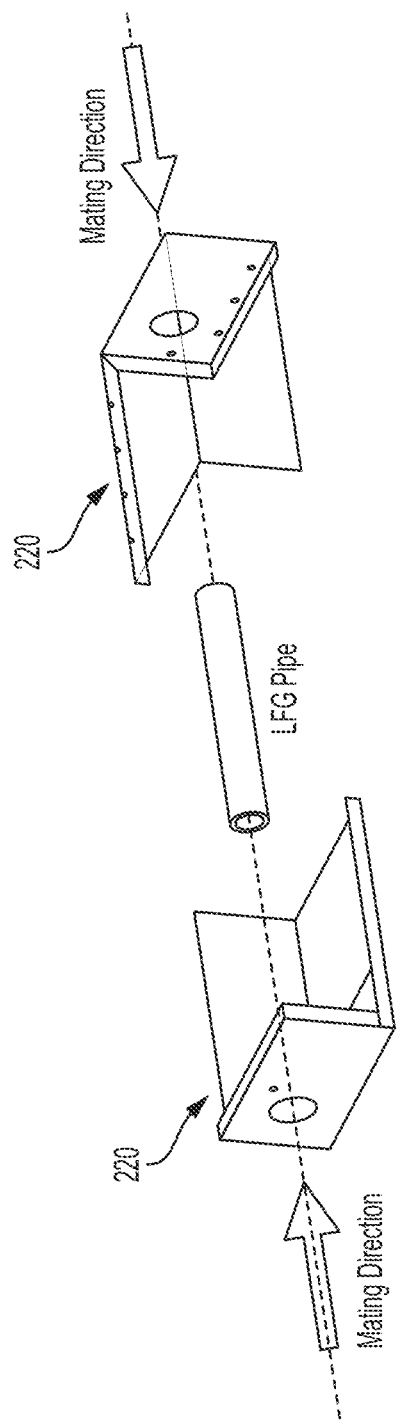
FIG. 14 is a diagram illustrating assembling an enclosure with an internally-routed LFG stream, according to some embodiments.

Some embodiments may employ an insulated and/or air-tight or sealed enclosure (such as enclosure 220 shown in FIGS. 2, 14, and 15) to retain heat within the enclosure.

Some embodiments may employ nonmetallic (or otherwise non-thermally conductive) mounting features, including but not limited to, standoffs or screws, to convey mechanical support through the insulation to the enclosure or structures outside of the enclosure to reduce thermal shorts associated with these voids in the insulation.

Some embodiments may be designed to route the warm LFG gas stream, specifically a pipe (such as pipe 210 shown in FIG. 2) carrying the warm LFG stream, through the enclosure of some embodiments to provide a passive heat source within the enclosure.

Figure 15:
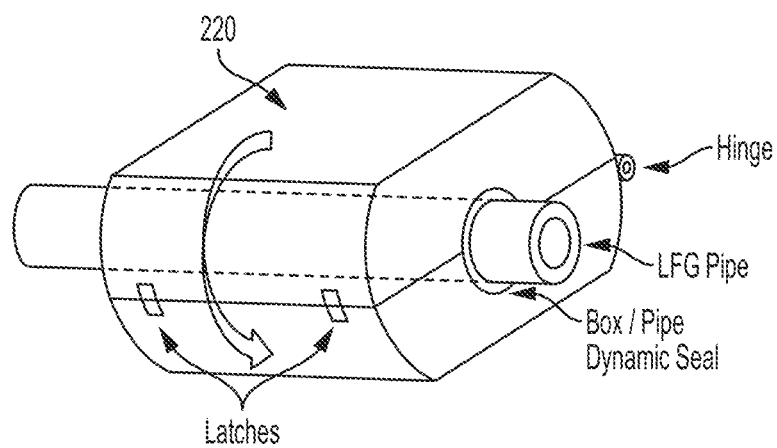
FIG. 15 is a sketch illustrating a clamshell-style enclosure with internally-routed LFG stream, according to some embodiments.

In some embodiments, the enclosure may carefully be designed in such a way as to accommodate for the pipe carrying the LFG stream in a manner conducive to improved manufacturability and serviceability. For instance, cutouts in a simple box with a lid may be less advantageous than designing the enclosure to part in the direction axially with the pipe, or part in a clamshell style radially with the pipe, as shown in FIG. 15.

In some embodiments, the enclosure may be designed with special features to independently seal against the enclosure and the pipe to promote easier assembly and serviceability. Examples of static and dynamic seals 162, 160 are illustrated in FIGS. 15 and 16.

In some embodiments, this pipe may be constructed from a chemically compatible metal, such as stainless steel, to enhance thermal conduction from the warm LFG gas stream to the inside of the box. Alternatively, this pipe may be constructed from a chemically compatible plastic, such as CPVC, with lower thermal conductivity than a corresponding metal pipe to reduce cost or weight or improve manufacturability.

According to some embodiments, the unit 200 may include at least one thermal conductivity component 290 configured to enhance a thermal conductivity of the section 215 of the pipe 210. For example, the thermal conductivity component 290 may be a corrosion resistant metal heat sink 290, such as that shown in FIG. 7. Alternatively or additionally, the unit 200 may include at least one fan configured to circulate air across the section 215 of the pipe 210. For example, FIG. 7 illustrates a fan with the heat sink 290, although the fan could be positioned in any suitable way.

Figure 17:
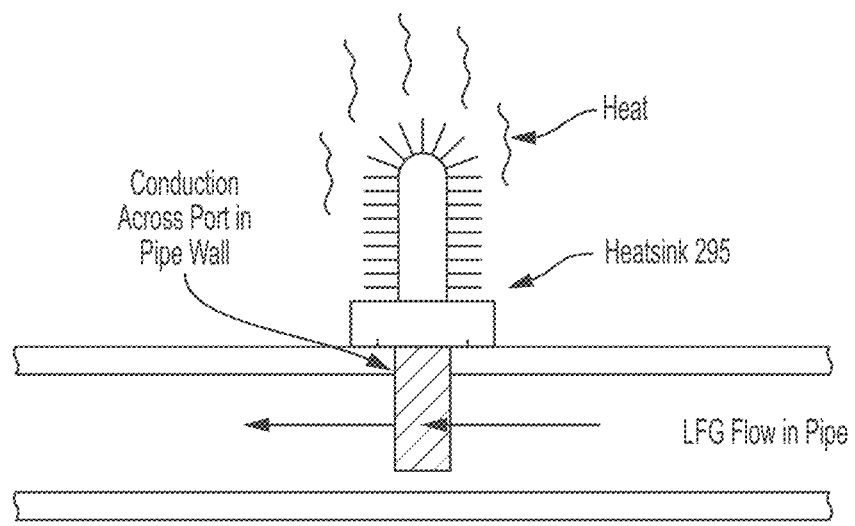
FIG. 17 is a sketch illustrating a component for conducting heat into the enclosure, according to some embodiments.
Figure 18:
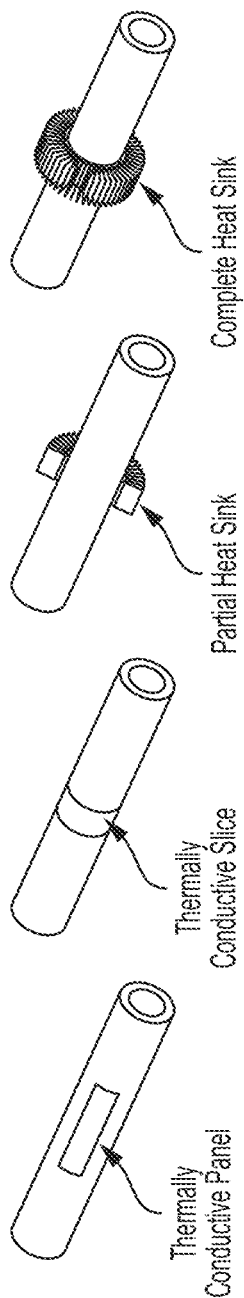
FIG. 18 is a collection of sketches illustrating multiple features that may be added to the pipe, according to some embodiments.

For example, in some embodiments, thermally conductive features may be added to the plastic pipe to enhance thermal conductivity, although some such features may be used with other materials of pipe. In some embodiments, a corrosion resistant metal heat sink may be inserted into the LFG gas stream through a sealed port in the pipe wall, or a segment of the plastic pipe maybe replaced with a segment of corrosion resistant metal—both acting to conduct heat from the gas stream across the pipe wall into the enclosure. Examples of heat sinks in some embodiments are shown in FIGS. 17 and 18.

In some embodiments, the LFG gas stream may be directed through a component that has the purpose of conducting heat from the LFG gas stream into the enclosure. Additionally, this component may be an orifice plate (such as that shown in FIG. 12) that, while normally used for flow measurement, is also designed to conduct heat from the LFG stream into the enclosure.

In some embodiments, devices or features may be added to the pipe (metal or plastic) carrying the LFG gas stream to improve convection. For instance, heat sink fins, thermally conductive panels, and/or thermally conductive slices (such as shown in FIG. 18) may be added to the pipe providing increased passive convection from the pipe wall. Similarly, a fan may be added to circulate air inside the enclosure across the pipe, providing forced convection from the pipe wall.

According to some embodiments, the unit 200 may include at least one active heating element 285 configured to emit heat within the enclosure 220. Additionally, the unit 200 may include at least one controller 275 configured to control the at least one active heating element 285.

For example, some embodiments may employ active heating elements 285 within the enclosure at the cost of an increased power budget. In some embodiments, a control system may be used to regulate the power, duty cycle or other signal driving the forced convection or heating element.

In some embodiments, this control system may operate as a closed-loop thermostat using a combination of some or all measurements including, but not limited to, the internal box temperature, LFG gas stream temperature, available battery charge or available power supply voltage as feedback. For instance, the control system may try to maintain a specific or minimum internal box temperature, but optimize performance based on the available thermal capacity of the LFG stream or power budget.

In some embodiments, a system level controller 275 governing a plurality of units may be used independently or in conjunction with the individual temperature controllers in each unit to optimize power budget for heating use during current or forecasted cold weather. For instance, reducing frequency of measurement cycles or otherwise throttling back auxiliary power consumption could save energy to instead be used for heating.

In some embodiments, a system level controller 275 may be used independently or in conjunction with the individual temperature controllers in each unit to optimize power budget (potentially, but not necessarily, for heating use) during periods of reduced battery charging by reducing frequency of measurement cycles or otherwise throttling back auxiliary power consumption. For instance, a cloudy forecast could prompt the controller 275 to signal solar-recharged units to reduce power consumption until the dawn of a sunnier day.

In some embodiments, the thermal mitigation strategy may be optimized by calculating the relative gains and losses in thermal impedance for varying enclosure insulation thicknesses and material types, active and passive heating capacities, and the relative tradeoffs against constraints such as, but not limited to, size, cost, and weight. For instance, calculations and empirical results may indicate that adding an extra inch of insulation may be less effective at keeping some embodiments warm than adding forced air convection to the pipe carrying the LFG stream.

In some embodiments, the active heating element may be the waste heat from another system, such as the hot side of a thermoelectric condenser used in gas sample filtration.

Simplifying Hardware Installation and Maintenance

Site Installation and Mounting Considerations

Some embodiments may be designed to mate with existing infrastructure most commonly found at a landfill wellfield, such as vacuum hoses, wellheads, or elastomeric reducing couplings.

According to some embodiments, the unit 200 may include at least one adjustable mounting apparatus configured to mount the enclosure 220 to at least one of an existing well riser pipe and/or an existing well head 104.

According to some embodiments, at least one end of the pipe 210 may include a shape configured to couple with an existing well riser pipe, an existing well head 204, an existing vacuum hose, and/or an existing elastomeric reducing coupling. For example, the shape may comprise at least one taper.

According to some embodiments, mounting features on some embodiments may be designed in such a way allow for cantilevering off of an existing wellhead or well riser. Alternatively or additionally, mounting features on some embodiments may be designed in such a way allow for vertical mounting such that the mounting feature runs parallel to the gas flow path.

In some embodiments, this mounting feature or strut may be banded, clamped, or strapped to the corresponding well or vacuum riser to provide support when some embodiments—specifically one end of the LFG-carrying pipe running through the unit—are installed directly into the elastomeric coupling.

In some embodiments, it may be advantageous to use a specially tapered installation plug to cap the vacuum coupling during installation, reducing the likelihood of excess atmosphere/oxygen entering the extraction system.

In some embodiments, when one end of the LFG-carrying pipe is installed directly into the elastomeric coupling, the other end of the LFG-carrying pipe may be connected directly to the vacuum hose.

In some embodiments, when one end of the LFG-carrying pipe is connected directly to the vacuum hose, clamps, bands or straps may be used to tighten around the hose to make a seal to the LFG-carrying pipe.

Some embodiments, when designed primarily for this vertical mounting scheme, may be adapted using one or more fittings and lengths of hose to allow the device to mate with unions present on the existing system—in particular, those found on wellheads.

Some embodiments may be designed to work best when installed at a slight angle in relation to the gas stream. For instance, if an eccentric orifice plate is used, the optimal installation may be one that angles the flow direction so that condensate preferentially streams along the wall nearest the orifice bore and away from the pressure or sampling ports.

In some embodiments, the mounting feature on the device enclosure may feature a "T" configuration as in the figure below. Such a configuration may allow the installation of the device on a riser pipe that comes out of the ground at an angle, while preserving a desired orientation with respect to gravity or another reference.

In some embodiments, the ends of the pipe carrying the LFG stream that runs through the enclosure may be tapered to provide for easier insertion into mating connections on the system vacuum or extraction point connections, easing system installation.

In some embodiments, mounting features on the enclosure may be designed in such a way to also function as a handle or handles used when carrying and installing at the site, easing the deployment process.

Some embodiments may feature a handle or handles independent of mounting features used to carry and install at a site, easing the deployment process.

Designs and Methods for Field Serviceability

In some embodiments, the enclosure may be designed with a front panel allowing for service of one or more components.

In some embodiments, the orifice plate, orifice plate lid, and orifice slot may be designed to slide in through a slot accessible through this front panel.

In some embodiments, the gas sampling system may be arranged in such a way to allow access to the calibration port 239 from this front panel.

In some embodiments, this front panel may contain a user interface consisting of buttons and a text or graphic display that interfaces with the internal electronics.

In some embodiments, this user interface can be used to toggle unit commands including, but not limited to, initiating measurement cycles, initiating calibration cycles, changing valve command, opening a connection to the server or initiating a purge command (for purging all fluid paths with clean air before the unit is uninstalled and removed from the LFG stream).

In some embodiments, the filtration system may employ a sensor in line with the sample gas to measure characteristics after the filter such as, but not limited to, humidity or hydrogen sulfide content to provide a gauge of filter health. For instance, as the adsorbent media meant to filter hydrogen sulfide is consumed, the sensor after the filter may register a higher concentration of hydrogen sulfide, eventually indicating that it is time to change the filter.

Some embodiments may incorporate one or more water detection or moisture sensors within the box to alert a technician of a failure in the filter system or presence of a leak.

Some embodiments may be assembled with a vapor corrosion inhibitor that deposits a corrosion inhibiting layer on exposed components within the enclosure.

In some embodiments, the gas sensor chamber may be assembled with a vapor corrosion inhibitor that deposits a corrosion inhibiting layer on the gas sensors.

Some embodiments may be assembled with desiccant to absorb any water vapor in the box introduced during assembly or maintenance access, preventing condensation on interior surfaces or electronics.

Figure 19:
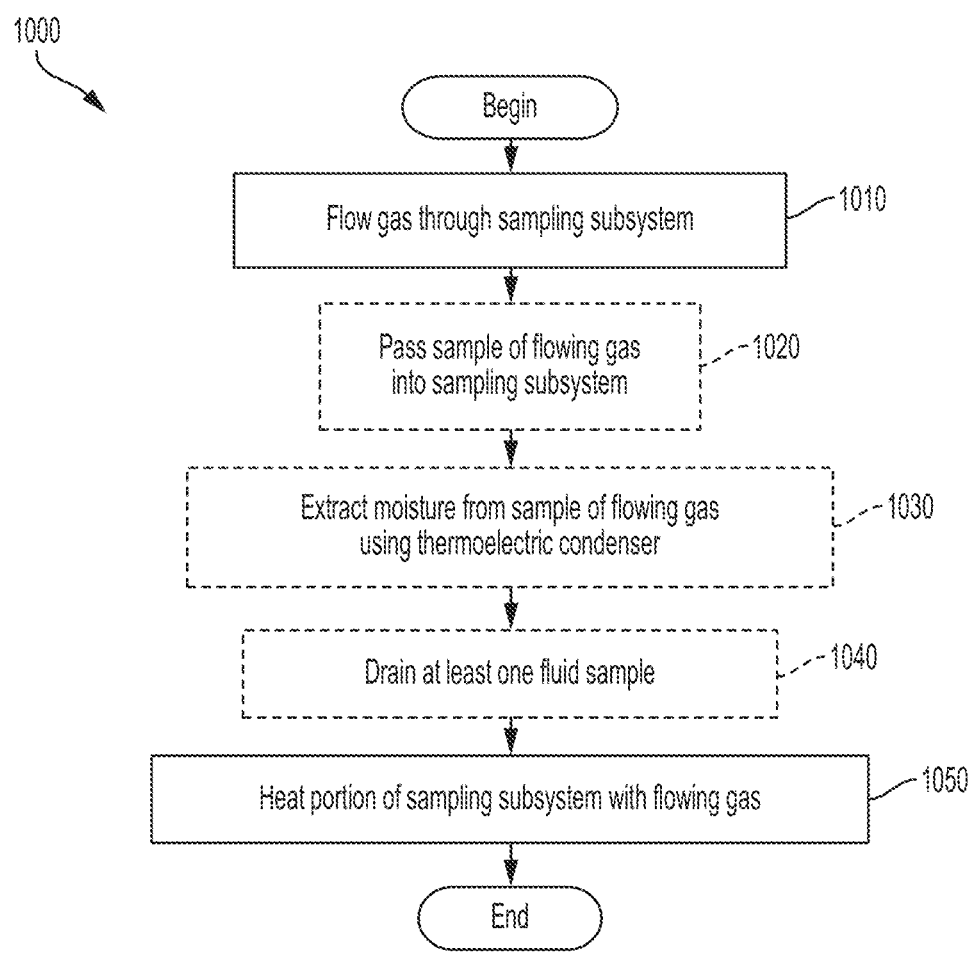
FIG. 19 is a flowchart of a method for flowing gas, according to some embodiments.

FIG. 19 illustrates a flowchart of an exemplary process 1000 of using a unit, such as unit 200, in some embodiments. The process 1000 begins at stage 1010. At stage 1010, gas may be flowed through a sampling subsystem 225 from a well riser pipe to a collection system, such as collection system 110 shown in FIG. 1. This flow may be achieved in any suitable way, including by opening a valve that enables gas to flow from the landfill or by active control of a vacuum, as is known in the art.

The process 1000 may optionally proceed to stage 1020. At stage 1020, a sample of the flowing gas may be passed into a sampling subsystem 225, such as by controlling valves or otherwise enabling gas to flow into a unit 200.

The process 1000 may optionally proceed to stage 1030. At stage 1030, moisture may be extracted from the sample of the flowing gas using a thermoelectric condenser, such as the thermoelectric condenser 234.

The process 1000 may optionally proceed to stage 1040. At stage 1040, at least one fluid is drained from the sample of the flowing gas using at least one fluid knock-out, such as the at least one fluid knock-out 232.

The process 1000 may then proceed to stage 1050. At stage 1050, a portion of the sampling subsystem 225 may be heated with the gas flowing from the well riser pipe to the collection system. The process 1000 may then end for a given sample. The process 1000 may be continued or repeated any number of times for other samples or for periodic or even continuous monitoring.

One or more aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the application may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An apparatus for sampling landfill gas flowing through a pipe, the apparatus comprising:
   an enclosure configured for coupling to a section of the pipe, the section of the pipe having at least one gas sampling port;
   at least one sensor device disposed in a region of the enclosure, the at least one sensor device being coupled to the section of the pipe through the at least one gas sampling port; and
   at least one controller configured to:
      adjust a frequency of landfill gas sampling based at least in part on an available battery charge and/or an available power supply voltage of the apparatus, wherein adjusting the frequency of landfill gas sampling comprises adjusting a frequency of operation of at least one pump for pumping landfill gas from the pipe to the region of the enclosure having the at least one sensor device such that the at least one pump continues to pump the landfill gas into the region of the enclosure, but at a reduced frequency.

2. The apparatus of claim 1, wherein the enclosure comprises an hermetic seal.

3. The apparatus of claim 1, further comprising:
   thermal insulation positioned to retain heat from the section of the pipe.

4. The apparatus of claim 3, further comprising:
   at least one thermal conductivity component configured for enhancing a thermal conductivity of the section of the pipe.

5. The apparatus of claim 4, wherein the thermal conductivity component comprises a corrosion resistant metal heat sink.

6. The apparatus of claim 3, further comprising:
   at least one active heating element configured to emit heat within the enclosure wherein
   the at least one controller is configured to control the at least one active heating element.

7. The apparatus of claim 1, wherein the at least one sensor device comprises:
   a sensor configured to measure flow of the landfill gas through the pipe and a sensor configured to measure characteristics of a gas sample.

8. The apparatus of claim 1, wherein the at least one sensor device comprises:
   a sensor configured to measure humidity of the landfill gas.

9. The apparatus of claim 1, comprising:
   a sampling subsystem comprising:
      a gas inlet port and a gas outlet port, wherein the at least one sensor device is coupled to the gas outlet port;
      the region of the enclosure, the region of the enclosure further being configured to be coupled to the section of the pipe having the at least one gas sampling port;
      a thermoelectric condenser; and
      a gas flow passage from the gas inlet port, over the at least one sensor device, and to the gas outlet port, the gas flow passage passing adjacent to and in thermal contact with the thermoelectric condenser.

10. The apparatus of claim 9, wherein:
    the thermoelectric condenser comprises at least one channel at a surface of a block.

11. The apparatus of claim 10, wherein:

the thermoelectric condenser is covered by at least one chilled plate, and the at least one channel is configured to direct a gas sample across the at least one chilled plate.

12. The apparatus of claim 9, wherein:

the at least one sensor device is a gas sensor disposed in the region of the enclosure and coupled to the section of the pipe through the at least one gas sampling port; and the apparatus further comprises thermal insulation positioned to retain heat from the section of the pipe in the region of the enclosure.

13. The apparatus of claim 9, wherein:

the sampling subsystem comprises an orifice block and a filter for at least one of a particulate and a corrosive gas, and the gas flow passage comprises at least one fluid knockout.

14. The apparatus of claim 9, wherein:

the at least one sensor device comprises a pressure sensor and a sensor configured to measure an amount of gas of a predetermined type.

15. The apparatus of claim 1, wherein the enclosure is configured to receive the section of the pipe.

16. The apparatus of claim 1, further comprising a wireless transmitter.

17. A method performed by an apparatus for sampling landfill gas flowing through a pipe, the apparatus comprising an enclosure for coupling to a section of the pipe, the section of the pipe having at least one gas sampling port, at least one sensor device disposed in the enclosure and coupled to the section of the pipe through the at least one gas sampling port, a wireless transmitter, and a controller, the method comprising:

obtaining at least one measurement, using the at least one sensor device, of a concentration of at least one constituent gas in the landfill gas flowing through the pipe;

transmitting, using the wireless transmitter, the at least one measurement obtained by the at least one sensor device to an external device; and adjusting a frequency of landfill gas sampling based at least on an available battery charge and/or an available power supply voltage of the apparatus, wherein adjusting the frequency of landfill gas sampling comprises adjusting a frequency of operation of at least one pump for pumping landfill gas from the pipe to a region of the enclosure having the at least one sensor device such that the at least one pump continues to pump the landfill gas into the region of the enclosure, but at a reduced frequency.

18. The method of claim 17, wherein the enclosure is configured to receive the section of the pipe.

19. An apparatus for sampling landfill gas flowing through a pipe, the apparatus comprising:

an enclosure configured for coupling to a section of the pipe, the section of the pipe having at least one gas sampling port;

at least one sensor device disposed in a region of the enclosure, the at least one sensor device being coupled to the section of the pipe through the at least one gas sampling port; and at least one controller configured to:

adjust a frequency of landfill gas sampling based at least in part on a temperature inside the enclosure and/or landfill gas temperature, wherein adjusting the frequency of landfill gas sampling comprises adjusting a frequency of operation of the at least one sensor device such that the at least one sensor device continues to perform the landfill gas sampling, but at a reduced frequency.

20. The apparatus of claim 19, wherein the at least one controller is configured to adjust the frequency of landfill gas sampling at least in part by decreasing the frequency of landfill gas sampling in response to a decrease in the temperature inside the enclosure.

* * * * *